US012751911B2

(12) United States Patent
Fevola et al.

(10) Patent No.: US 12,751,911 B2
(45) **Date of Patent: *Oct. 6, 2026**

(54) LOW VISCOSITY NONAQUEOUS METAL OXIDE PARTICLE DISPERSIONS

(71) Applicant: Inolex Investment Corporation, Wilmington, DE (US)

(72) Inventors: Michael J. Fevola, Wilmington, DE (US); Tobias J. Fütterer, Wilmington, DE (US); Brittany M. Pease, Wilmington, DE (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 245 days.

This patent is subject to a terminal disclaimer.

(21) Appl. No.: 18/490,956

(22) Filed: Oct. 20, 2023

(65) Prior Publication Data

US 2024/0173243 A1 May 30, 2024

Related U.S. Application Data

(60) Provisional application No. 63/422,063, filed on Nov. 3, 2022, provisional application No. 63/422,057, filed on Nov. 3, 2022.

(51) Int. Cl.

| | |
|---|---|
| ***A61K 8/85*** | (2006.01) |
| ***A61G 17/04*** | (2006.01) |
| ***A61K 8/06*** | (2006.01) |
| ***A61K 8/27*** | (2006.01) |
| ***A61K 8/29*** | (2006.01) |
| ***A61Q 17/04*** | (2006.01) |
| ***C08J 3/20*** | (2006.01) |
| ***C08K 3/22*** | (2006.01) |

(52) U.S. Cl.

CPC ................ *A61K 8/85* (2013.01); *A61G 17/04* (2013.01); *A61K 8/06* (2013.01); *A61K 8/062* (2013.01); *A61K 8/064* (2013.01); *A61K 8/27* (2013.01); *A61K 8/29* (2013.01); *C08J 3/203* (2013.01); *C08K 3/22* (2013.01); *C08J 2367/04* (2013.01); *C08K 2003/2237* (2013.01); *C08K 2003/2296* (2013.01)

(58) Field of Classification Search

None

See application file for complete search history.

(56) References Cited

U.S. PATENT DOCUMENTS

| | | | | |
|---|---|---|---|---|
| 2008/0299057 | A1* | 12/2008 | Lin | A61Q 17/04 424/59 |
| 2011/0150792 | A1 | 6/2011 | Shao et al. | |
| 2012/0003287 | A1 | 1/2012 | Schlossman et al. | |
| 2012/0219515 | A1* | 8/2012 | Barrett | A61K 8/817 424/59 |
| 2014/0030339 | A1 | 1/2014 | Leblanc et al. | |
| 2021/0059924 | A1* | 3/2021 | Croom | A61K 8/85 |

FOREIGN PATENT DOCUMENTS

| | | | | |
|---|---|---|---|---|
| EP | 3884927 | A1 | 9/2021 | |
| WO | 1996041614 | A1 | 12/1996 | |
| WO | WO-2010019939 | A1 * | 2/2010 | C07C 69/533 |
| WO | 2010068687 | A1 | 6/2010 | |
| WO | 2022129192 | A1 | 6/2022 | |
| WO | WO 2022187271 | A1 | 9/2022 | |

OTHER PUBLICATIONS https://www.healthchems.com/Products/Polyhydroxystearic-Acid-180772.html, retrieved Sep. 28, 2025.*

Safety Assessment of Polyhydroxystearic Acid, Poly(3-Hydroxyoctanoic Acid), and Polylactic Acid as Used in Cosmetics , CIR Report Data Sheet , 2022.*

English Translation of WO 2010/019939 (Year: 2010).*

Nascimento, et al.; "Characterization and Evaluation of Poly(epsilon-caprolactone) Nanoparticles Containing 2-Ethylhexyl-p-Methozycinnamate, Octocrylene, and Benzophenon-3 in Anti-Solar Preparations", Journal of Nanoscience and Nanotechnology, 2012, vol. 12, 1-12, expecially: abstract; p. 7, Table III.

International Search Report and Written Opinion for PCT/US23/77380; Dated Apr. 11, 2024; ISA/US.

(Continued)

*Primary Examiner* — David J Blanchard
*Assistant Examiner* — Sarah J Chickos
(74) *Attorney, Agent, or Firm* — COZEN O'CONNOR

(57) ABSTRACT

The present invention relates to a nonaqueous composition for dispersing metal oxide particles. The nonaqueous composition comprises a dispersing media comprising esters with branched or unsaturated alkyl chains, preferably synthesized from 100% biobased carbon, and a polyester dispersing agent that includes a terminal carboxylic acid functional group. The ester dispersing media includes a liquid ester selected from the group consisting of: Formulas (I), (II), (III), and combinations thereof. The present invention also relates to a nonaqueous dispersion comprising the nonaqueous composition above and metal oxide particles dispersed therein. The metal oxide particles may comprise zinc oxide, titanium oxide, or combinations thereof. Formulations using the compositions and dispersions as well as processes for preparing are also disclosed.

24 Claims, 1 Drawing Sheet

(56) References Cited

OTHER PUBLICATIONS

International Search Report and Written Opinion for PCT/US23/77381; Dated Apr. 15, 2024; ISA/US.
Acure® Radically Rejuvenating SPF Day Cream, Mintel Global New Products Database, Record ID: 7277485, published Feb. 2020, https://www.gnpd.com/sinatra/recordpage/7277485.
Acure® Seriously Soothing SPF Day Cream. Mintel Global New Products Database, Record ID: 6787469, published Aug. 2019, https://www.gnpd.com/sinatra/recordpage/6787469.
Examination Report No. 1, dated Jul. 22, 2025 from Australian Government, IP Australia, Contact: Joseph Ambrush—CHEM 5—Pharmaceuticals for Australian Appl. No. 2023374554 following ISR for WO2024/097540.
Database GNPD [Online] "MINTEL"; Jul. 1, 2021, "Cream Blush", XP093369868, Database accession No. 8775789.
Database GNPD {Online] "MINTEL"; Aug. 12, 2014, "Eco-Bio Face & Body Milk for Baby & Kids SPF 30", XP093369151, Database accession No. 2597849.
Database GNPD {Online] "MINTEL"; Jul. 12, 2019, "Cusion SPF 50+ PA++++", XP093369986, Database accession No. 6699595.

* cited by examiner

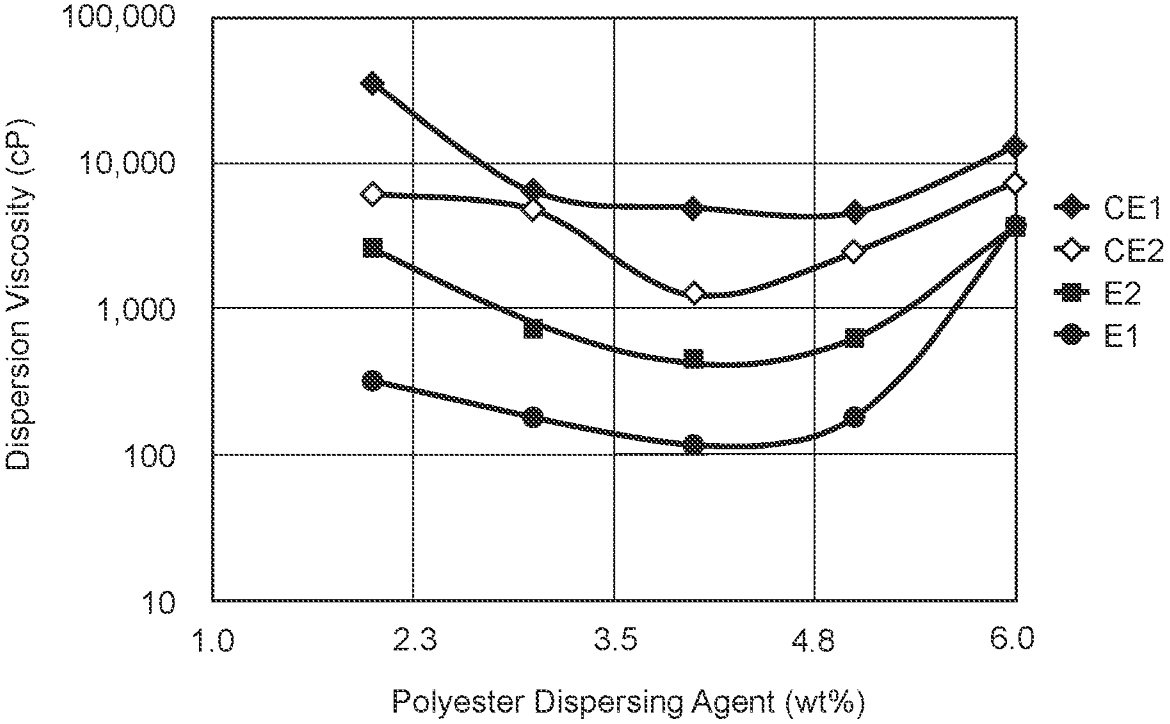
100,000
10,000
1,000
100
10
Dispersion Viscosity (cP)
1.0
2.3
3.5
4.8
6.0
Polyester Dispersing Agent (wt%)
CE1
CE2
E2
E1

LOW VISCOSITY NONAQUEOUS METAL OXIDE PARTICLE DISPERSIONS

CROSS REFERENCE TO RELATED APPLICATIONS

This Application claims priority to U.S. Provisional Application No. 63/422,063, filed Nov. 3, 2022, and U.S. Provisional Application No. 63/422,057, filed Nov. 3, 2022, which are each incorporated herein by reference.

FIELD OF INVENTION

The present invention relates to compositions, dispersions, and formulations comprising nonaqueous ester dispersing media and polyester dispersing agents, optionally in combination with metal oxide particles, and processes for preparing and using the compositions to prepare dispersions, and formulations, and applications thereof that include inter alia personal care applications, e.g., suncare formulations.

BACKGROUND OF THE TECHNOLOGY

Inorganic metal oxides, e.g., zinc oxide (ZnO) and titanium dioxide ($TiO_2$), are important sunscreen ingredients due to their ability to absorb and/or scatter UVB and UVA radiation, thus providing protection against sunburn and photodamage that can lead to premature aging and/or skin cancer. These metal oxides are most desirably supplied as sub-micron sized particles that do not scatter visible wavelengths of light on the skin and thus do not cause the appearance of whitening on the skin. The metal oxide particles ("MOP") are typically prepared and supplied as free-flowing powders.

To effectively prepare sunscreen formulations containing ZnO and/or $TiO_2$ MOPs that provide adequate sun protection factor ("SPF") values and that are non-whitening on skin requires creating dispersions of the MOPs that are stable against agglomeration.

Creation of a dispersion involves employing high shear mixing or milling to mechanically disrupt and disperse the powdered and/or any agglomerated MOPs into a liquid medium, i.e. the dispersing medium. Dispersing media can be either aqueous or nonaqueous in nature. Wetting of the MOPs by the dispersing medium forms a dispersed homogeneous state that typically requires a dispersing agent to prevent reagglomeration of the MOPs. [See, e.g., C. Agbo et al., *A Review on the Mechanism of Pigment Dispersion*, J. Disp. Sci. Tech., 2018, 39(6), 874-889.]

The MOPs are preferably dispersed in nonaqueous fluids that are easily applied to skin and possess consumer acceptable tactile properties on skin. Nonaqueous dispersion media for MOPs such as ZnO and $TiO_2$ include a wide variety of cosmetically acceptable fluids that are typically used as emollients in cosmetics and personal care products. Examples of such fluids include aliphatic hydrocarbons, triglycerides, benzoate esters, aliphatic esters, or combinations thereof, as well as silicone fluids such as cyclomethicones and dimethicone.

Given ever increasing consumer preference for more natural and sustainable products, the nonaqueous dispersing media are preferably derived from sustainable, renewable, plant-based feedstocks. An example of a naturally-derived dispersing medium is caprylic/capric triglyceride, a triglyceride synthesized by the complete esterification of vegetable glycerin with a mixture of $C_8$ (caprylic) and $C_{10}$ (capric) fatty acids derived from either coconut or palm kernel oil. Other examples of plant-derived biobased nonaqueous dispersing media include plant-derived oils, e.g., *Simmondsia chinensis* (jojoba) seed oil or *Helianthus annus* (sunflower) seed oil; fermentation-derived hydrocarbons, e.g., hydrogenated farnesene; hydrocarbons derived from triglyceride oils (via hydrolysis to fatty acids, reduction to fatty alcohol, and dehydration/hydrogenation to hydrocarbon), e.g., coconut alkanes; and esters derived from plant-based saturated fatty acids and saturated fatty alcohols, e.g., coco-caprylate/caprate derived from the esterification of hydrogenated coconut fatty alcohol with $C_8/C_{10}$ fatty acids.

Obtaining stable dispersions of MOPs in nonaqueous media typically requires surface modification of the particles to render the hydrophilic inorganic surface hydrophobic so that it is compatible with the relatively nonpolar dispersing medium, i.e., so that the nonaqueous dispersing liquid can wet the MOP surface. Such surface modification can be achieved through the use of hydrophobic coatings that adhere to the MOP surface through physical and/or covalent interactions. Examples of surface modifying agents for use with MOPs include fatty acids (e.g., isostearic acid), trialkoxylalkylsiloxanes, (e.g., triethoxycaprylsilane), or silicones (e.g., methicone or dimethicone). Surface modification of MOPs typically entails an additional process step and/or unit operation to properly apply the surface treatment, see e.g., U.S. Pat. No. 9,254,398 B2. Therefore, it is more efficient and economical to develop dispersion systems that can employ non-surface treated, i.e. uncoated MOPs.

It is desirable to create flowable, low-viscosity particle dispersions having high loadings of MOPs, which can minimize the carryover of excess dispersing medium into subsequent formulations to which a particular MOP dispersion is added. However, conventional triglyceride dispersing media (e.g. caprylic/capric triglycerides and triheptanoin) typically yield MOP dispersions with undesirably high viscosities when formulated at MOP loadings having a solid particle volume fraction greater than about 50%. See, e.g., D. A. Brune et al., Model for the Viscosity of Particle Dispersions; Journal of Macromolecular Science—Rev. Macromol. Chem. Phys., C39(4), 561-642 (1999). Thus, to obtain stable, yet pourable MOP dispersions with these triglycerides, it is unfortunately necessary to decrease the particle loading.

Additionally, the use of a dispersing agent to provide steric stabilization against particle agglomeration in nonaqueous dispersing media is required. Polymeric dispersing agents are common, and polyhydroxystearic acid is a well-known dispersing agent for ZnO and $TiO_2$ MOPs. [See, e.g., B. J. Naden et al. *Adsorption of poly(hydroxystearic acid) to $TiO_2$ nanoparticles, studied using gel permeation chromatography*, Coll. Surf. A.: Physicochem. Eng. Aspects, 2015, 478, 36-44.]

Such nonaqueous dispersions are preferably of a low viscosity (i.e., less than about 1000 cP) so that they are easy to prepare and handle in subsequent formulation steps, and the dispersed solid particles must remain stable in the dispersion for prolonged periods. Low viscosity dispersions are also desirable when formulated into sunscreen products, as they provide for products that are more easily dispensed and applied by the consumer.

Thus, there exists a need for stable, low viscosity, high-solids dispersions of MOP. The nonaqueous compositions should be preferentially based on renewable carbon sources, i.e., plant-based carbon, due to the market demand for more sustainable ingredients and greater consumer appeal of so-called "natural" ingredients derived from renewable, biobased feedstock. Particularly, the need exists for nonaqueous compositions comprising one or more dispersing agents prepared from renewable, biobased carbon, more preferably 100% biobased carbon.

BRIEF SUMMARY OF THE INVENTION

The nonaqueous compositions described and claimed herein satisfy these long-felt needs and comprise an ester dispersing medium (EDM) and a carboxylic acid-terminated polyester, to which MOP(s) can be added to provide a homogeneous MOP dispersion.

Applicants have discovered surprisingly that a dispersing medium comprising a branched or unsaturated ester, preferably synthesized from 100% biobased carbon as described herein, provides stable MOP dispersions with exceptionally low viscosities at relatively high particle loadings. Thus, stable, low viscosity, high-solids MOP dispersions using dispersing media and dispersing agents based on 100% natural and renewable carbon are achieved. And the ester can be combined with readily available polyester dispersing agents (PEDAs) where the suitability is not dependent upon molecular weight distribution, i.e., low and high molecular weight polyesters perform well with the branched or unsaturated esters described herein.

In some embodiments, the present invention is directed to a nonaqueous composition. The nonaqueous composition comprises an ester and a polyester having a terminal carboxylic acid functional group. The ester is selected from the group consisting of:

(i) a liquid ester of Formula I:

I

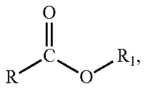

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

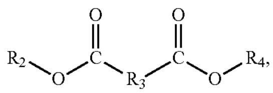

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

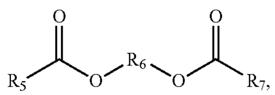

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof.

The ester of the nonaqueous composition as in the preceding paragraph may be of Formula I and R is a $C_5$-$C_{17}$ branched or cyclic alkyl, linear, branched, or cyclic alkenyl, or linear, branched, or cyclic alkynyl; and $R_1$ is a $C_3$-$C_{18}$ linear, branched, or cyclic alkyl, linear, branched, or cyclic alkenyl, or linear, branched, or cyclic alkynyl. The ester of Formula I may include that R and $R_1$ are different.

The ester of the nonaqueous composition as in any of the preceding paragraphs may be of Formula II and $R_2$ is a $C_3$-$C_{18}$ branched alkyl, linear or branched alkenyl, or linear or branched alkynyl; $R_3$ is a $C_2$-$C_8$ linear or branched alkyl, linear or branched alkenyl, or linear or branched alkynyl; and $R_4$ is a $C_3$-$C_{18}$ linear or branched alkyl, linear or branched alkenyl, or linear or branched alkynyl. The ester of Formula II may include that $R_2$ and $R_4$ are the same.

The ester of the nonaqueous composition as in any of the preceding paragraphs may be of Formula III and $R_5$ is a $C_3$-$C_{18}$ branched alkyl, linear or branched alkene, or linear or branched alkyne, $R_6$ is a $C_2$-$C_8$ linear or branched alkyl, linear or branched alkene, or linear or branched alkyne, and $R_7$ is a $C_3$-$C_{18}$ linear or branched alkyl, linear or branched alkene, or linear or branched alkyne. The ester of Formula III may include that $R_5$ and $R_7$ are the same.

The ester of the nonaqueous composition as in any of the preceding paragraphs may be liquid at 25° C. The ester may be 100% biobased.

The polyester of the nonaqueous composition as in any of the preceding paragraphs may comprise a terminal single carboxylic acid functional group. The polyester may comprise two terminal carboxylic acid functional groups.

The polyester of the nonaqueous composition as in any of the preceding paragraphs may comprise a homopolymer derived from AB hydroxycarboxylic acid monomers. The polyester may comprise a copolymer derived from AA diol and BB diacid or dibasic ester monomers.

The polyester of the nonaqueous composition as in any of the preceding paragraphs may have a number-average molecular weight ($M_n$) of less than about 10,000 g/mol. The polyester may have an Acid Value of at least 15 mg KOH/g.

The polyester of the nonaqueous composition as in any of the preceding paragraphs may be selected from the group consisting of: Polyhydroxystearic Acid, Polyhydroxystearic Acid Stearate, Polyhydroxystearyl Succinate, Polyhydroxystearyl Sebacate, and combinations thereof. Carbon present in the polyester may be 100% biobased.

In particular embodiments, the present invention is directed to a nonaqueous composition consisting essentially of:

an ester selected from the group consisting of:

(i) a liquid ester of Formula I:

I

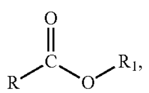

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

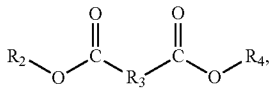

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

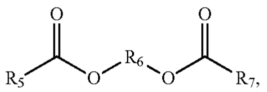

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof;

and a polyester having a terminal carboxylic acid functional group.

In other particular embodiments, the present invention is directed to a nonaqueous composition consisting of:

an ester selected from the group consisting of:

(i) a liquid ester of Formula I:

I

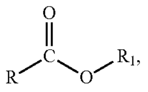

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

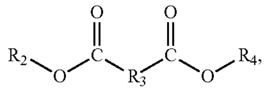

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

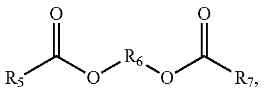

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof;

and a polyester having a terminal carboxylic acid functional group.

In other embodiments, the present invention is directed to a nonaqueous dispersion comprising a nonaqueous composition and a metal oxide particle powder. The nonaqueous composition for the nonaqueous dispersion may be according to the nonaqueous composition as in any of the preceding paragraphs.

The metal oxide particles for the nonaqueous dispersion as in the preceding paragraph may include metal oxide particles that are not surface-modified, e.g., particles devoid of surface modification.

The metal oxide particles for the nonaqueous dispersion as in any of the preceding paragraphs may include zinc oxide, titanium oxide, or combinations thereof.

The nonaqueous dispersion as in any of the preceding paragraphs may have a viscosity of less than about 1000 cP. The metal oxide particles may comprise about 15 wt % to about 75 wt % of the nonaqueous dispersion, the balance being the nonaqueous composition as in any of the preceding paragraphs. In some embodiments, the metal oxide particles comprise about 40 wt % to about 60 wt % of the nonaqueous dispersion. The polyester may be present in an amount of about 3 wt % to about 5 wt % based on total weight of the dispersion. The nonaqueous dispersion may be substantially devoid of silicones.

In particular embodiments, the present invention is directed to a nonaqueous dispersion comprising:

a composition comprising:

an ester selected from the group consisting of:

(i) a liquid ester of Formula I:

I

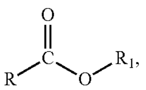

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

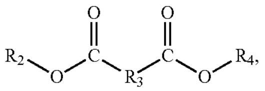

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

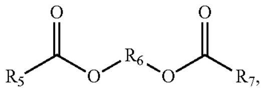

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof;

and a polyester having a terminal carboxylic acid functional group; and a plurality of metal oxide particles dispersed in the composition.

In yet other embodiments, the present invention is directed to a formulation comprising a nonaqueous composition or a nonaqueous dispersion as in any of the preceding paragraphs. The formulation may be or may be a component of a personal care product selected from the group consisting of: a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer. The formulation may be or may be a component of a sunscreen. The formulation may be an oil-in-water (O/W) emulsion or a water-in-oil (W/O) emulsion. The formulation may further comprise at least one additional ingredient selected from the group consisting of film-forming polymers, rheology modifying polymers, waxes, emulsifiers, emollients, humectants, and combinations thereof.

The present invention is further directed to a process for preparing a nonaqueous composition for dispersing a metal oxide particle powder. The process comprises:

mixing:

an ester selected from the group consisting of:

(i) a liquid ester of Formula I:

I

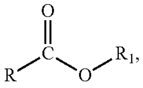

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

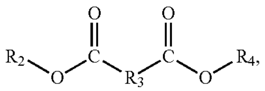

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

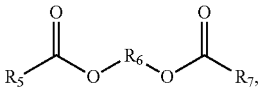

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof; and a polyester having a terminal carboxylic acid functional group to form a homogeneous solution.

The process may include an ester as in any of the preceding paragraphs, e.g., an ester of Formula I, Formula II, Formula III, and combinations thereof. The process may include a polyester as in any of the preceding paragraphs.

Mixing of the process to form a homogeneous solution may include heating. Mixing of the process may include high-shear mixing.

The process may further include dispersing metal oxide particles in the homogeneous solution to form a nonaqueous dispersion. The metal oxide particles of the process may include metal oxide particle as in any of the preceding paragraphs.

The process may further include adding at least one additional ingredient therein to form a formulation. The at least one additional ingredient may be selected from the group consisting of film-forming polymers, rheology modifying polymers, waxes, emulsifiers, emollients, humectants, and combinations thereof. The formulation of the process may be a sunscreen.

BRIEF DESCRIPTION OF THE FIGURES AND DRAWINGS

FIG. 1 illustrates dispersion viscosities as function of polyester concentration for Examples E1-E2 according to embodiments herein and Comparative Examples CE1-CE2.

DETAILED DESCRIPTION

Before the present compounds, compositions, and methods, among others, are described, it is to be understood that this invention is not limited to the particular processes, compositions, or methodologies described, as these may vary. It is also to be understood that the terminology used in the description is for the purpose of describing the particular versions or embodiments only and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

Unless specified, "%" can refer to either a percent by weight or volume.

Unless specified, room temperature can refer to about 25° C., or 25° C., or in a range from 22.5° C. to 27.5° C., or in a range from 20° C. to 30° C.

Where applicable, notation such as $C_x$-$C_y$ denotes a range for the number of carbons and includes $C_x$ and $C_y$ and all the groups in between. For example, $C_5$-$C_9$ includes each of the groups pentyl, hexyl, heptyl, octyl, and nonyl.

"Cosmetically acceptable" means suitable for use in contact with the skin without undue toxicity, incompatibility, instability, irritation, allergic response, and the like.

Where applicable, chemicals are specified by their INCI Name according to the guidelines of the International Nomenclature of Cosmetic Ingredients. Additional information, including suppliers and trade names, can be found under the appropriate INCI monograph in the International Cosmetic Ingredient Dictionary and Handbook, 16th Edition published by the Personal Care Products Council, Washington, DC, or online in the Personal Care Products Council INCIpedia (https://incipedia.personalcarecouncil.org/).

Among the many embodiments, the present invention includes biobased compositions. Biobased or "natural" feedstocks must be used in the production of biobased compositions. An example of a biobased composition is one that is prepared from a bioderived feedstock (e.g., from current and sustainable agricultural activities, such as fermentation-, algae-, plant- or vegetable-derived; e.g., is derived from a vegetable source, preferably using a non-genetically modified organism, or biomass, and it is not petrochemically-derived (such as being derived from sustainable tree and plant farms active in the 21st century vs. fossil sources such as petroleum, natural gas, or coal). Such feedstocks are referred to herein as "natural" and "renewable" (i.e., "sustainable") and are known in the art as a non-petroleum-derived feedstock. Further, such materials are formed by "new" carbon and not from petroleum or other fossil fuel sources ("old" carbon). Such products are referred to herein as "natural" products and are known in the art as non-petrochemically-derived or "bio" products. As used herein, the term "sustainable" refers to starting materials, reaction products, compositions, and/or formulations that are derived from renewable sources. The term "sustainable" therefore is in contrast to "non-sustainable" starting materials, reaction products, compositions, and/or formulations that contain carbon from a limited natural resource, such as fossil fuel (e.g., petroleum or coal), natural gas, and the like. Thus, a natural or bio product is not petrochemically derived and/or is made from a source that is not petrochemically derived, but rather are sustainable and renewable. True natural products (bio-compounds) are formed using biomass (e.g., material stored from carbon cycle processes in living plants, roots, and the like, or released through animal respiration or refuse, or through decomposition). When carbon decomposes and is broken down over millions of years under pressure, it creates fossil fuels (the source of petrochemically-derived carbon). Bio-compounds herein are intended to include materials derived from the carbon of plant sources/biomass that exist(ed) recently and/or are sustainable, and explicitly excludes materials derived from fossil fuels.

To distinguish a petroleum-based product from a truly natural and/or sustainable product, one must test for the authenticity using established and credible test methods. Current methods employ a detailed analysis of stable isotopes using mass spectroscopy and evaluating carbon-12/carbon-13 and/or hydrogen-1/hydrogen-2 ratios. Such testing is available through several analytical service testing organizations and is much faster, more cost effective, and yields more detailed information compared to radiocarbon testing methods.

Stable isotope analysis is based on the principle of kinetic isotope effect. The latter effect is well-known to those in the art of chemical kinetics. In the broadest terms, heavy isotopes of a particular element react slower than their lighter equivalent (e.g., carbon-12 as opposed to carbon-13). So, as plants incorporate carbon dioxide into their biomass, the ratio of carbon-12 to carbon-13 will vary depending on the type of chemistry used in the plant to make biomass (e.g., whether the plant undergoes a $C_3$ or $C_4$ photosynthesis pathway). This is commonly reported as the $\delta^{13}C/^{12}C$ ratio (i.e., $\delta^{13}C$), and is referenced to a current carbon dioxide standard. In addition, similar isotope kinetic effects are observed when water is incorporated into new biomass, and this is measured as the $\delta^{2}H/^{1}H$ ratio (i.e., $\delta^{2}H$). Using a combination of $\delta^{13}C$ and $\delta^{2}H$ ratios, one familiar with in the relevant art is able to readily distinguish and validate the nature of the feedstock that was used to prepare the product being analyzed (i.e., whether it is petrochemically-derived or derived from recently living or living algae-, plant- or similar bio-sources).

A composition and/or formulation of the present invention can be identified and distinguished from prior art compositions and/or formulations by its biobased carbon content. In some embodiments, the biobased carbon content can be measured by radiocarbon dating to determine the relative age of materials comprised of organic (i.e., carbon-containing) matter. Radiocarbon is an unstable isotope of carbon, known as Carbon-14 (i.e., "$^{14}C$"). $^{14}C$ is an unstable isotope that emits radiation energy in the form of beta particles at a very consistent rate (i.e. a half-life for radiocarbon is 5730 years) and ultimately decays to the more stable Nitrogen-14 ($^{14}N$). Because, petroleum-based (i.e. petrochemically-derived) feedstocks are derived from plants and animals buried millions of years ago, such feedstocks' radiocarbon (i.e., $^{14}C$) has been lost to radioactive decay. The ASTM International standards provide testing standards to determine the authenticity of a "bio-based compound" using radiocarbon, which may be found in ASTM D6866-16. This standard distinguishes newer carbon from carbon derived from fossil-fuel, or petroleum- and petrochemically-derived sources, i.e., "old carbon". The amount of $^{14}C$ in recent or current biomass is known, so a percentage of carbon from a renewable source can be estimated from a total organic carbon analysis, which provides the data necessary to determine if a compound is truly derived from a "natural" and/or "sustainable" ("renewable") feedstock source or is derived conversely from a compound of "old" sequestration (i.e., a petrochemically-derived or petroleum-based source). The use of petroleum-based (also termed "fossil-based") feedstocks is generally accepted as being non-sustainable, i.e., old carbon is a non-sustainable and not a renewable feedstock and furthermore is not considered "natural" and/or "sustainable" in the art.

In some embodiments, the formulations and/or compositions of the present invention comprise biobased carbon as substantially all of the carbon present in the mixtures of compounds, which can refer to a biobased carbon content of at least 90%, at least 95%, or at least 98%.

In some embodiments, the compositions of the present invention comprise a $^{14}C$ content that is substantially equivalent to the present-day atmospheric $^{14}C$ content, as determined according to ASTM D6866. In some embodiments, the compositions of the present invention comprise a $^{14}C$ content that is at least about 90%, at least about 95%, at least about 98%, or at least about 99% of the present-day atmospheric $^{14}C$ content, as determined according to ASTM D6866. In some embodiments, the compositions of the present invention comprise at least about 0.8 $^{14}C$ atoms per $10^{12}$ carbon atoms present in the composition, at least about 1.0 $^{14}C$ atoms per $10^{12}$ carbon atoms present in the composition, or at least about 1.2 $^{14}C$ atoms per $10^{12}$ carbon atoms present in the composition, as determined according to ASTM D6866.

By "sustainable" herein, the applicants refer to materials derived from renewable sources. In contrast "non-sustainable" refers to materials from a limited natural resource, such as a fossil fuel (e.g., petroleum, natural gas, coal, and the like).

Introduction

The present invention relates to nonaqueous compositions including an ester dispersing medium (EDM) and a carboxylic acid-terminated polyester, to which MOP(s) can be added to provide a homogeneous MOP dispersion. The ester may be the EDM and the polyester may be the polyester dispersing agent (PEDA). As detailed above, stable, low viscosity, high-solids dispersions of MOPs using dispersing media and dispersing agents based on 100% natural and renewable carbon are achieved. Applicants have surprisingly discovered that dispersing media comprised of esters with branched or unsaturated alkyl chains, preferably synthesized from 100% biobased carbon, as described herein provide stable dispersions with exceptionally low viscosities at relatively high particle loadings. The esters described are other than fully saturated, linear esters, i.e., compounds comprising only saturated linear esters are not included herein.

Nonaqueous Dispersions.

Inventive nonaqueous compositions herein include an EDM (comprising an ester containing a branched alkyl group or an unsaturated alkyl group) and a carboxylic acid-terminated PEDA. Metal oxide particles are added to the nonaqueous compositions herein to form homogeneous nonaqueous dispersions.

The non-aqueous compositions of the present invention provide an "off-the-shelf" dispersion system that enables low-viscosity dispersions to be formed with a wide range of metal oxide particles. In particular, users of the non-aqueous dispersions need not have specialized mixing equipment or experience making stable non-aqueous dispersions.

In some embodiments, the nonaqueous compositions of the present invention consist essentially of (i) one or more liquid esters having a branched alkyl group or an unsaturated alkyl group and (ii) a carboxylic acid-terminated polyester polymer. The basic and novel properties of such inventive compositions include the capability of forming stable, low-viscosity nonaqueous dispersions with a wide variety of metal oxide particles. In addition, the nonaqueous compositions described herein demonstrate ease in processing due, at least in part, to the low viscosities realized.

Metal Oxide Particles.

Some embodiments herein are directed to dispersion compositions including metal oxide particles. The MOPs are preferably solid, white (or colorless), odorless metal oxide particles. MOPs herein may comprise zinc oxide (ZnO) and/or titanium dioxide ($TiO_2$) particles. These are particularly useful in formulations such as sunscreen. Some dispersions and/or formulations herein may additionally or alternatively comprise metal oxides that include one or more of iron, copper, manganese, magnesium, cerium, vanadium, zirconium, aluminum, silicon, e.g., FeO, $Fe_2O_3$, $Fe_3O_4$, $CeO_2$, $V_2O_5$, $ZrO_2$, $MnO_2$, MgO, $Al_2O_3$, $SiO_2$, CaO, or combinations thereof and other cosmetically acceptable metal oxides. Suitable metal oxides also include doped metal oxides (e.g., doped with any of the aforementioned metals and metal oxides). Other suitable metal oxide particles include coated particles (e.g., coated with any of the aforementioned metals and metal oxides). The MOPs are of high purity, e.g., greater than 95%, greater than 96%, greater than 97%, greater than 98%, or greater than 99%.

In some embodiments, the surface of the metal oxide particles may be modified. Such surface modification, especially in case of $TiO_2$, can suppress photocatalytic activity in subsequent formulations. Inorganic coatings, e.g., alumina or silica, are preferably used for any surface modification.

Alternatively, organic surface modification, while less preferable, can be acceptable. Surface modification with organic or hybrid organic-inorganic coating derived from fossil-based carbon is undesirable due to poor sustainability profile and poor consumer acceptance. Specifically, surface modification with silicones or siloxanes is less preferred. For example, trialkoxylalkylsiloxanes, e.g. triethoxycaprylsilane, or silicones, e.g., methicone or dimethicone, and the like are less preferred due to negative environmental impact and/or negative consumer perception.

Any coating or surface modification of particles such as described above is included as part of the mass or weight of the particles, e.g., MOPs, herein.

MOPs without surface modification may also be used in compositions and formulations described here. In some embodiments, uncoated metal oxide particles are preferred. In certain embodiments, MOPs comprising uncoated ZnO are used in compositions and formulations described herein.

The average particle size of the MOPs is non-limiting, however, the average particle size of the MOPs may preferably be sub-micron in diameter. The metal oxide particles can, for example, be present in a composition in a range of average particle size from 10 nm to 500 nm, e.g., from 10 nm to 400 nm, from 20 nm to 300 nm, or from 30 nm to 150 nm. In terms of upper limits, the average particle size of the MOPs may be less than 500 nm, e.g., less than 400 nm, less than 300 nm, or less than 150 nm. In terms of lower limits, the average particle size of MOPs may be greater than 10 nm, e.g., greater than 20 nm or greater 30 nm. In preferred embodiments, the average particle size of the MOPs is less than about 200 nm. These ranges and limits may be applicable to formulations including these compositions as well.

The MOPs used in compositions, dispersions, and formulations described herein may exhibit a broad average particle size distribution range. The average particle size distribution can, for example, range from about 10 nm to about 500 nm, e.g., from 10 nm to 400 nm, from 20 nm to 300 nm, or from 30 nm to 150 nm. In preferred embodiments, the average particle size distribution ranges from about 30 nm to about 150 nm. The particles may be present as clusters or agglomerates. The MOPs can exhibit particle shapes chosen from spherical, rod-like, star-like, isometric, spherical, plate-like, platelet, or combinations thereof. In some preferred embodiments, the MOPs, e.g., ZnO particles are characterized as having a variety of shapes. [See, e.g., *Zinc oxide* (*nano form*); *What are the properties of ZnO nanoparticles*?, https://ec.europa.eu/health/scientific_committees/opinions_layman/zinc-oxide/de/1-3/3.htm#.]

In some or other embodiments, the MOPs can be added to a nonaqueous composition to form a dispersion. In other words, nonaqueous compositions including an ester dispersing medium and a carboxylic acid-terminated polyester dispersing agent as described herein are provided directly or subsequently adding the MOP to form a dispersion and/or a formulation thereof.

Ester Dispersing Media.

A nonaqueous composition for dispersing metal oxide particles, as well as dispersions and formulations herein, include a nonaqueous ester dispersing medium (EDM). "Ester dispersing medium" or simply "ester" as used interchangeably herein are esters that have physical properties suitable for use as dispersing medium, e.g., the esters are liquid (at room temperature, e.g., 25° C.) and/or the esters have a viscosity that is less than about 100 cSt at 25° C. Esters suitable as ester dispersing medium include branched or unsaturated esters as detailed below.

In aspects herein, the esters include one or more of the R groups selected such that the ester will be a liquid at 25° C.

As contemplated herein, inventive compositions, dispersions, and formulations may contain other esters (that are not EDMs as defined herein) in addition to the ester dispersing medium. The non-EDM esters that could be present include waxy esters for structuring formulations and films, enhancing water repellency, and the like. Examples of non-EDM esters include, but are not limited to, Hydrogenated Rapeseed Oil, Jojoba Esters, Hydrogenated Jojoba Oil, Synthetic Beeswax.

Inventors have found surprisingly that a dispersing medium comprising branched or unsaturated esters are suitable in nonaqueous compositions for MOPs dispersions due to the ability to lower the viscosity of said compositions in combination with a polyester dispersing agent (PEDA as described below).

Preferably, the nonaqueous composition comprises an ester having a branched alkyl group or an unsaturated alkyl group. For purposes herein, a branch point may be defined with respect to any carbon or heteroatom in the molecule or may also refer to a stereocenter. For example, in certain embodiments the methyl branch is located at the 1-position, e.g., the methyl branch is located on the carbon atom bearing the hydroxyl group of the alcohol such as 1-methylheptyl alcohol, as shown below:

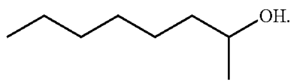

In some embodiments, the nonaqueous composition for dispersing metal oxide particles comprises a liquid ester of Formula I:

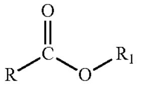

I wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl. In some embodiments, R is a $C_5$-$C_{17}$ branched or cyclic alkyl, linear, branched, or cyclic alkenyl, or linear, branched, or cyclic alkynyl; and $R_1$ is a $C_3$-$C_{18}$ linear, branched, or cyclic alkyl, linear, branched, or cyclic alkenyl, or linear, branched, or cyclic alkynyl. In some embodiments, the ester is of Formula I and R and $R_1$ are different. In some embodiments, R is preferably $C_{10}$ unsaturated. R is even more preferably $C_{10}$ terminal unsaturated. In some embodiments, $R_1$ is preferably $C_6$-$C_{12}$ linear saturated. $R_1$ is even more preferably $C_7$-$C_8$ linear saturated.

An example ester according to Formula (I) includes Heptyl Undecylenate (LexFeel® Natural, INOLEX Inc.) according to the structure (I-i):

(I-i)

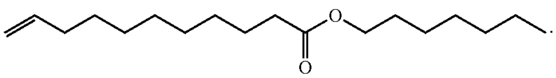

In addition to heptyl undecylenate as described above, other example esters include octyl undecylenate and/or decyl undecylenate.

In other embodiments, the nonaqueous composition for dispersing metal oxide particles comprises a liquid ester of Formula (II):

(II)

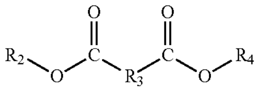

wherein $R_2$ is wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl. In some embodiments, $R_2$ is a $C_3$-$C_{18}$ branched alkyl, linear or branched alkenyl, or linear or branched alkynyl, $R_3$ is a $C_2$-$C_8$ linear or branched alkyl, linear or branched alkenyl, or linear or branched alkynyl; and $R_4$ is a $C_3$-$C_{18}$ linear or branched alkyl, linear or branched alkenyl, or linear or branched alkynyl. In some embodiments, the ester is of Formula II and $R_2$ and $R_4$ are the same. In some embodiments, $R_2$ and $R_4$ are preferably branched $C_4$-$C_{18}$, more preferably branched $C_5$-$C_{18}$, even more preferably branched $C_6$-$C_{12}$. In some embodiments $R_3$ is preferably linear $C_2$-$C_8$.

An example ester according to Formula (II) includes Diisooctyl Succinate (SustOleo™ DCS, INOLEX Inc.) according to the structure (II-i):

(II-i)

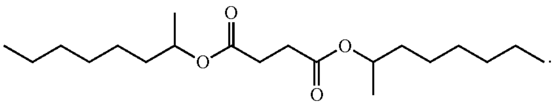

In other embodiments, the nonaqueous composition for dispersing metal oxide particles comprises a liquid ester of Formula (III):

(III)

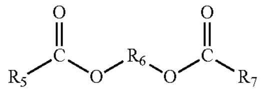

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne. In some embodiments, $R_5$ is a $C_3$-$C_{18}$ branched alkyl, linear or branched alkene, or linear or branched alkyne, $R_6$ is a $C_2$-$C_8$ linear or branched alkyl, linear or branched alkene, or linear or branched alkyne, and $R_7$ is a $C_3$-$C_{18}$ linear or branched alkyl, linear or branched alkene, or linear or branched alkyne. In some embodiments, the ester is of Formula III and $R_5$ and $R_7$ are the same.

Example esters according to Formula (III) include Propylene Glycol Diisostearate and Propylene Glycol Diundecylenate.

Nonaqueous compositions for dispersing metal oxide particles herein may comprise an ester selected from the group consisting of: (i) an ester of Formula I, (ii) an ester of Formula II, (iii) an ester of Formula III, and combinations thereof. In some embodiments, dispersions and/or formulations comprise an ester of Formula I, Formula II, Formula III, and combinations thereof. In some embodiments, dispersions and/or formulations comprise a liquid ester of Formula I, Formula II, Formula III, and combinations thereof. The ester of Formula I, Formula II, Formula III, and combinations thereof may have a viscosity of less than about 100 cSt at 25° C. Ester dispersing media herein include the esters as described above.

Other ester dispersing media or esters that are contemplated include nonaqueous ester comprising a triglyceride compound, such as the triglyceride compound of Formula (IV):

(IV)

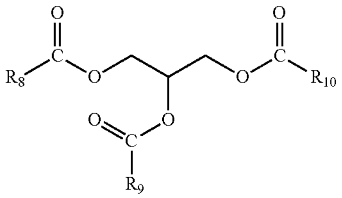

where $R_8$, $R_9$, and $R_{10}$ are each independently chosen from a linear, branched, saturated, or unsaturated alkyl group containing 5 to 18 carbon atoms ($C_5$-$C_{18}$). In some embodiments, two or more of $R_8$, $R_9$, and $R_{10}$ are the same. In some specific embodiments, $R_8$, $R_9$, and $R_{10}$ are unsaturated, branched, or have a double bond, or one of the $R_8$, $R_9$, and $R_{10}$ can be removed to form a diester.

However, these triglyceride esters (Formula IV) with $R_8$, $R_9$, and $R_{10}$ all being linear are comparative examples as described herein and include saturated triglycerides such as Triheptanoin and/or Caprylic/Capric Triglyceride.

One comparative example of an ester according to Formula (IV) includes Triheptanoin (SustOleo™ MCT, INOLEX Inc.), which is a non-palm, 100% natural medium chain triglyceride, according to the structure (IV-i):

(IV-i)

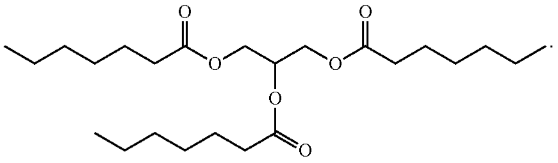

These triglyceride esters are not suitable in the nonaqueous compositions herein due to their high dispersion viscosities in combination with PEDAs according to the invention (and as detailed below in Table 2 and FIG. 1).

In some embodiments, the ester of the nonaqueous dispersions herein has a viscosity of less than about 100 cSt at 25° C. In preferred embodiments, the ester has a viscosity of less than about 50 cSt at 25° C. More preferred, the ester has a viscosity of less than 25 cSt at 25° C.

Carbon present in the esters as described above can be 100% biobased. In embodiments herein, the carbon atoms of the ester comprise greater than about 50%, e.g., greater than 70%, greater than 80%, greater than 90%, greater than 95%, or greater than 99% biobased carbon (as determined via $^{14}C$ radiocarbon dating as described above or other method known to those skilled in the art). In some embodiments, the ester comprises 100% biobased carbon. In some embodiments, substantially all of the carbon present in the compounds of Formulas (I), (II), (III), (IV), or combinations thereof is biobased. Preferred embodiments herein include that the ester dispersing medium comprises 100% biobased carbon.

The nonaqueous EDM may also optionally comprise one or more other nonaqueous organic fluids that are miscible with the primary ester component and acceptable for cosmetic use. Examples of suitable nonaqueous organic fluids include hydrocarbons, cyclic alkyl carbonates, dialkyl carbonates, dialkyl ketones, and the like.

By describing a composition and/or a dispersion herein as "nonaqueous" it is meant that the composition (and/or dispersion) is substantially free of added water, preferably containing less than about 3 wt % water, more preferably less than about 1 wt % water, even more preferably less than about 0.5 wt % water, and most preferably less than about 0.1 wt % water. Nonaqueous compositions (and/or dispersions) may contain minor amounts of incidental water (e.g., from absorption of ambient humidity) or processing conditions (e.g., washing followed by incomplete drying).

Polyester Dispersing Agents.

A nonaqueous composition for dispersing a metal oxide particle, as well as dispersions and formulations herein, may include a polyester dispersing agent. "Polyester dispersing agent" and "polyester" are used interchangeably herein, where the polyester dispersing agent (PEDA) herein is a polyester having a terminal carboxylic acid functional group and performs a specific function as described below.

As contemplated herein, inventive compositions may additionally include other polyesters (that are not PEDAs as defined herein) in addition to the PEDA. The additional non-PEDA polyesters may include, for example, polyester film formers for improving water resistance, among others.

The nonaqueous composition includes an aliphatic polyester that is insoluble in water. In some embodiments, the polyester is carboxy-functional, in other words, one or more chain ends are terminated with a carboxylic acid moiety. Polyesters herein have a terminal carboxylic acid functional group. Thus, polyesters as described herein are carboxylic acid-terminated polyester dispersing agents. For example, the polyester may comprise a terminal single carboxylic acid functional group or may comprise two terminal carboxylic acid functional groups.

The PEDAs may be characterized by Acid Value (as measured by AOCS Official Method Te 2a-64). In some embodiments, the PEDA has an Acid Value of at least 15 mg KOH/g. The Acid Value for the PEDA can, for example, range from about 15 mg KOH/g to about 100 mg KOH/g, e.g., from 20 mg KOH/g to 90 mg KOH/g, from 25 mg KOH/g to 80 mg KOH/g, or from 30 mg KOH/g to 75 mg KOH/g. The Acid value for the PEDA can, in terms of lower limits, be greater than about 15 mg KOH, e.g., greater than 20 mg KOH, greater than 25 mg KOH/g, or greater than 30 mg KOH/g. The Acid value for the PEDA can, in terms of upper limits, be less than about 100 mg KOH, e.g., less than 90 mg KOH, less than 80 mg KOH/g, or less than 75 mg KOH/g.

In some embodiments, the nonaqueous composition for dispersing MOPs for dispersions and/or formulations herein comprises a polyester homopolymer derived from condensation polymerization of a hydroxyalkanoic acid of Formula (V):

(V)

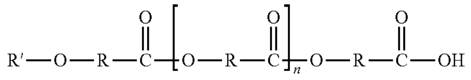

wherein R is chosen from a linear, branched, saturated, or unsaturated alkyl group containing 5 to 23 carbon atoms ($C_5$-$C_{23}$); and R' is chosen from H or a linear, branched, cyclic, saturated, or unsaturated alkyl or acyl group containing 1 to 22 carbon atoms ($C_1$-$C_{22}$).

Example polyesters according to Formula (V) include Polyhydroxystearic Acid (structure shown below in (V-i), Polyhydroxystearic Acid Stearate (polyhydroxystearic acid wherein some or all of the hydroxyl groups are reacted with stearic acid to yield stearate esters), Polyhydroxystearyl Succinate (polyhydroxystearic acid wherein some or all of the hydroxyl groups are reacted with succinic acid to yield succinate mono- and/or di-esters), and Polyhydroxystearyl Sebacate (polyhydroxystearic acid wherein some or all of the hydroxyl groups are reacted with sebacic acid to yield sebacate mono- and/or di-esters), Polyricinoleic Acid, and carboxy-terminal estolides derived from oleic acid, e.g., Coco-Oleate Estolides. The mono-esters of Polyhydroxystearyl Succinate and Polyhydroxystearyl Sebacate are illustrated in Figures V-ii and V-iii, respectively. The diesters of Polyhydroxystearyl Succinate and Polyhydroxystearyl Sebacate are illustrated in Figure V-iv, wherein $R_{10}$=succinoyl $[C(O)(CH_2)_2C(O)]$ or sebacoyl, $[C(O)(CH_2)_8C(O)]$ and $R_{11}$=$C_{17}H_{34}$.

(V-i)

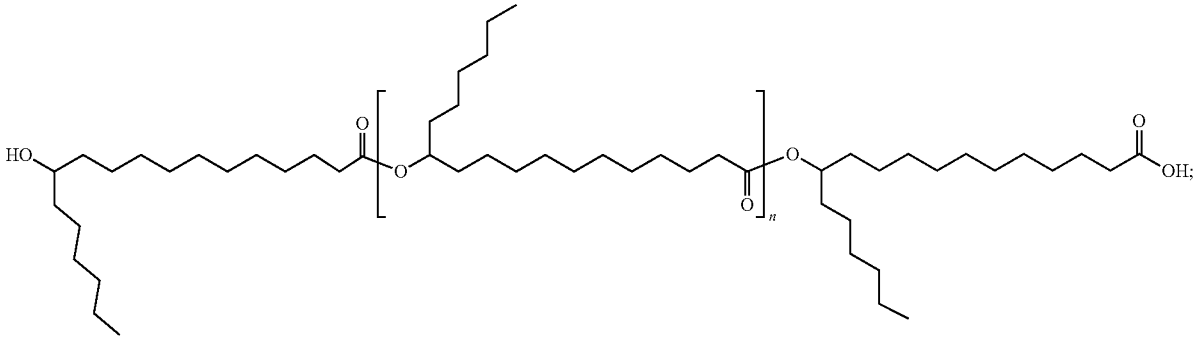

-continued (V-ii)

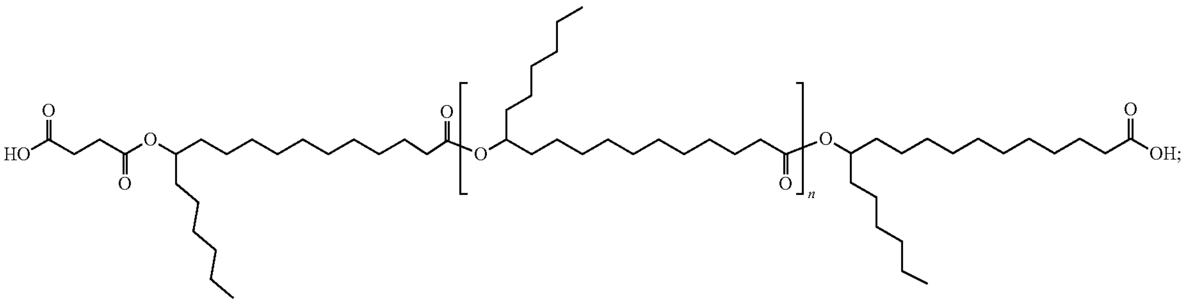

(V-iii)

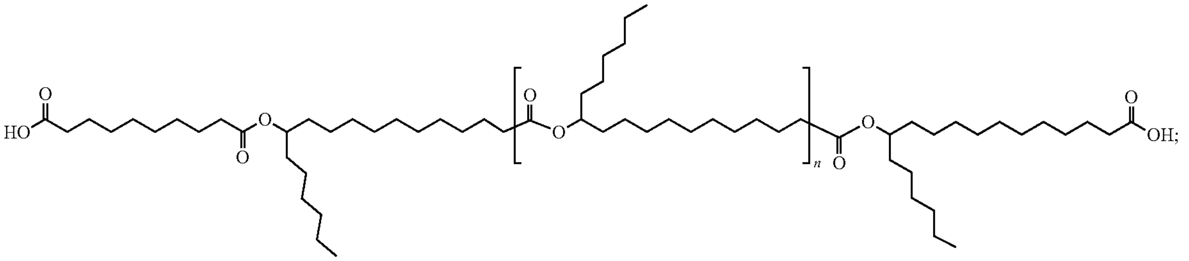

(V-iv)

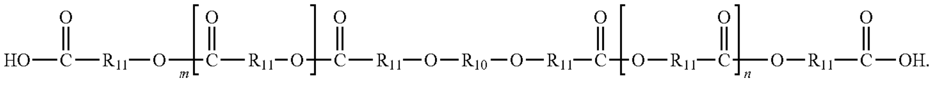

In some embodiments, the polyester may be a polyester copolymer derived from the condensation polymerization of two or more difunctional monomers, such as diols and diacids or dibasic esters (e.g. methyl esters), according to the structure (VI):

(VI)

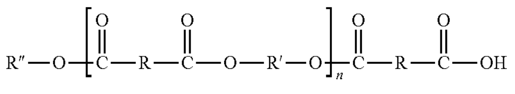

ester group at one end, but at least one chain end includes a carboxylic acid functionality. Alternatively, a hydroxy-functional polyester may be COOH end-capped, e.g. via post-polymerization reaction with an anhydride, e.g. succinic anhydride.

For example 1,2-pentanediol (pentylene glycol, R'=1,2-substituted n-pentyl) may be copolymerized with sebacic acid in a slight molar excess to yield carboxy-terminal telechelic (functionalized on both ends) poly(1,2-pentylene sebacate). An example polyester according to Formula (VI) includes Pentylene Glycol/Sebacic Acid Copolymer according to the structure (VI-i):

(VI-i)

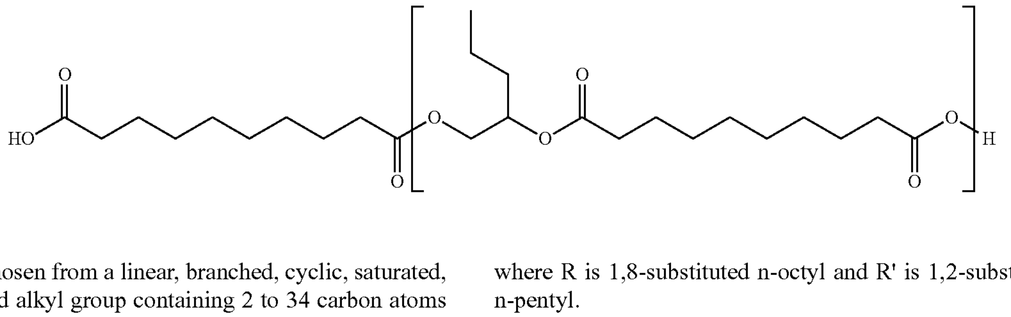

where R is chosen from a linear, branched, cyclic, saturated, or unsaturated alkyl group containing 2 to 34 carbon atoms ($C_2$-$C_{34}$); R' is chosen from a linear, branched, saturated, or unsaturated alkyl group containing 2 to 34 carbon atoms ($C_2$-$C_{34}$); and R" is chosen from H or a linear, branched, cyclic, saturated, or unsaturated alkyl or acyl group containing 1 to 22 carbon atoms ($C_1$-$C_{22}$). The acid functional monomers must be present in excess to ensure that the majority of polyester copolymer chain ends are carboxy-functional. The polyester copolymer may be capped with an where R is 1,8-substituted n-octyl and R' is 1,2-substituted n-pentyl.

In some embodiments, the carboxylic acid-terminated polyester dispersing agent comprises a linear polyester terminated with one carboxylic acid group. In other embodiments, the carboxylic acid-terminated polyester dispersing agent comprises a linear polyester terminated with two carboxylic acid groups, or a telechelic linear polyester terminated with carboxylic acid groups on both chain ends. In still other embodiments, the carboxylic acid-terminated polyester dispersing agent comprises a homopolymer derived from AB hydroxycarboxylic acid monomers. In yet other embodiments, the carboxylic acid-terminated polyester dispersing agent comprises a copolymer derived from AA diol and BB diacid or dibasic ester monomers. In preferred embodiments, the PEDA does not contain unsaturated moieties in the polymer backbone or as pendant groups, i.e. the PEDA does not contain C═C double bonds, which are susceptible to oxidative degradation.

The carboxylic acid-terminated polyester dispersing agent may be selected from the group consisting of Polyhydroxystearic Acid, Polyhydroxystearic Acid Stearate, Polyhydroxystearyl Succinate, Polyhydroxystearyl Sebacate, and combinations thereof.

Polyester dispersing agent as described above comprise biobased carbon. In embodiments herein, the carbon atoms of the polyester comprise greater than about 90%, e.g., greater than 95%, greater than 96%, greater than 97%, greater than 98%, or greater than 99% biobased carbon (as determined via $^{14}C$ radiocarbon dating as described above or other method known to those skilled in the art). In some embodiments, the polyester comprises 100% biobased carbon. In some embodiments, substantially all of the carbon present in the compounds of Formulas (V), (VI), or combinations thereof is biobased. The polyester is preferably comprised of renewable, biobased carbon. In preferred embodiments, the carboxylic acid-terminated polyester dispersing agent comprises 100% biobased carbon.

Preparation of Dispersions/Processes.

Nonaqueous dispersions herein can advantageously include a high loading of the metal oxide particles. The nonaqueous dispersions include a weight fraction of metal oxide particles in a range from about 15 wt % to about 75 wt % based on total weight of the nonaqueous dispersion, e.g., from 25 wt % to 75 wt %, from 30 wt % to 75 wt %, from 35 wt % to 75 wt %, from 40 wt % to 75 wt %, from 45 wt % to 75 wt %, from 50 wt % to 75 wt %, or from 40 wt % to 60 wt %. In terms of lower limits, the dispersion can include a metal oxide particle weight fraction of greater than 15 wt %, greater than 25 wt %, greater than 30 wt %, greater than 35 wt %, greater than 40 wt %, or greater than 45 wt %, or greater than 50 wt %. In preferred embodiments, the MOP fraction in the dispersion is greater than 40% wt % or greater than 45% wt %.

Nonaqueous dispersions herein desirably include a high loading of the metal oxide particles also in terms of volume fraction. The nonaqueous dispersions include a solid particle volume fraction of metal oxide particles in a range from about 20 vol % to about 80 vol % based on total volume of the nonaqueous dispersion, e.g., from 25 vol % to 75 vol %, from 30 vol % to 70 vol %, from 35 vol % to 70 vol %, from 40 vol % to 70 vol %, from 45 vol % to 65 vol %, or from 50 vol % to 65 vol %. In terms of lower limits, the dispersion can include a metal oxide particle volume fraction of greater than 20 vol %, greater than 25 vol %, greater than 30 vol %, greater than 35 vol %, greater than 40 vol %, greater than 45 vol %, or greater than 50 vol %. In preferred embodiments, the MOP fraction in the dispersion is greater than 50% vol %, greater than 60% vol %, or greater than 70% vol %.

The level (or concentration) of polyester in the dispersion is selected to yield the lowest range of dispersion viscosities possible. These dispersions include polyester in a range from about 1.00 wt % to about 10.00 wt % based on total weight of the dispersion (EDM+PEDA+MOPs), e.g., from 1.00 wt % to 7.00 wt %, from 2.00 wt % to 6.00 wt %, from 2.50 wt % to 5.50 wt %, or from 3.00 wt % to 5.00 wt %. In preferred embodiments, dispersion compositions include polyester in a range from 3.00 wt % to 5.00 wt %. The level of polyester required to achieve a stable, low viscosity dispersion will generally increase as the loading of MOP in the dispersion is increased. At the preferred level of polyester ranging from 3.00 wt % to 5.00 wt %, the MOPs loading is 50.05 wt % based on total weight of the dispersion, with the EDM present in the dispersion at an amount to total q.s. 100 wt %.

Processes herein include preparing a nonaqueous composition for dispersing metal oxide particles. In some embodiments, the process includes adding one or more components to the nonaqueous composition to form a nonaqueous dispersion and/or formulation.

Dispersions may be prepared according to any of the techniques familiar to those skilled in the art of pigment dispersions. The dispersion is preferably prepared by first preparing a nonaqueous composition. The nonaqueous composition may be prepared by dissolving the polyester in the ester, thus the PEDA in the EDM, to form a homogeneous solution.

Subsequently, the process includes adding the MOPs to the homogeneous solution (or mixture) with adequate mixing and shear to ensure a homogeneous nonaqueous dispersion. Heating may be applied to improve dissolution of the polyester in the ester. In addition to, or alternatively to, heating, high-shear mixing using a rotor-stator homogenizer, Cowles blade, colloid mill, or other high-shear device is performed to ensure optimum dispersion and stabilization of the MOPs.

In some embodiments, the process includes mixing EDM and a polyester having a terminal carboxylic acid functional group (PEDA) to form a homogeneous solution (or mixture). The EDM is selected from the group consisting of: (i) a liquid ester of Formula I, (ii) a liquid ester of Formula II, (iii) a liquid ester of Formula III, and combinations thereof. The ester(s) have been described above in detail. The process may include the ester having a viscosity of less than about 100 cSt at 25° C. The carbon present in the ester is 100% biobased.

The polyester may comprise a terminal single carboxylic acid functional group. In other embodiments, the process includes that the polyester comprises two terminal carboxylic acid functional groups.

The process may include the polyester having a number-average molecular weight ($M_n$) of less than about 10,000 g/mol. The polyester may have an Acid Value of at least 15 mg KOH/g. The process may include the polyester is chosen from the group consisting of Polyhydroxystearic Acid, Polyhydroxystearic Acid Stearate, Polyhydroxystearyl Succinate, Polyhydroxystearyl Sebacate, and combinations thereof. The carbon present in the polyester is 100% biobased.

Nonaqueous dispersions as described herein preferably exhibit low viscosities for ease of processing, e.g., mixing, pumping, etc., handling, and application. In some embodiments, the process includes wherein the nonaqueous dispersion has a viscosity of less than about 1000 cP. The dispersion compositions have a viscosity, in terms of upper limits, of less than about 1000 cP, e.g., less than 1000 cP, less than 900 cP, less than 750 cP, less than 500 cP, less than 300 cP, or less than 200 cP. These viscosities for the nonaqueous dispersions include MOPs.

These low viscosity nonaqueous metal oxide particle dispersions have a ratio of inorganic solid particulate, the metal oxide particles, to the nonaqueous composition ester-polyester mixture (homogeneous solution) ranging from about 1 to 0.33 (1:0.33) to about 1 to 5 (1:5) on a weight basis. In preferred embodiments, the nonaqueous dispersion has a ratio of inorganic particulate to ester-polyester mixture from about 1 to about 0.67 (1:0.67). In more preferred embodiments, the nonaqueous dispersion has a ratio of inorganic particulate to ester-polyester mixture from about 1 to about 1 (1:1). The ester-polyester mixture is the nonaqueous composition including EDM and PEDA.

Nonaqueous dispersions as described herein do not include silicones, e.g., the low viscosity nonaqueous metal oxide particle dispersion is substantially devoid of silicones.

Nonaqueous dispersions should demonstrate stability upon preparation, which means no settling, separation, or dramatic changes in viscosity should occur from the time of preparation to time of usage. This typically means that the dispersion is stable for days to weeks after preparation. The ability to easily redisperse settled solids by agitating a settled dispersion, e.g., with a mixer or shaker, is also a favorable indicator of dispersion stability, for example, in cases where lower solids loadings are desired such that there is insufficient colloidal packing and/or yield value present to prevent settling.

The process may include preparing the homogeneous solutions in advance so that the MOP can be added subsequently, i.e., the MOP component may be considered optional to be added later to form the nonaqueous dispersion. Thus the process may further include dispersing metal oxide particles in the mixture to form a nonaqueous dispersion. The metal oxide particles may comprise zinc oxide, titanium oxide, combinations thereof, as well as other metal oxides listed above.

The nonaqueous dispersion and formulations comprising the nonaqueous dispersions may be devoid of or substantially devoid of silicones, e.g., methicone, dimethicone, cyclopentasiloxane, and the like. "Silicone-free" compositions and formulations comprise less than about 1 wt %, preferably less than about 0.5 wt %, and more preferably less than about 0.1 wt % of silicone ingredients, or most preferably do not contain a measurable concentration or amount of a silicone.

The nonaqueous dispersions compositions may be used as-is or for the formulation of end products. For example, the dispersions may be formulated into various product formats such as oil-in-water (O/W) emulsions, water-in-oil (W/O) emulsions, creams, lotions, pastes, sprays, sticks, etc.

The process may further include adding at least one additional ingredient therein to form a formulation. The at least one additional ingredient is selected from the group consisting of film-forming polymers (such as Polyester-7, Polyester-10, Trimethylpentanediol/Adipic Acid/Glycerin Crosspolymer, Adipic Acid/Diglycol Crosspolymer, Ethyl Cellulose, Acrylates Copolymer such as Avalure™ AC series by Lubrizol, Polyurethane-62, PPG-17/IPDI/DMPA Copolymer), rheology modifying polymers (such as Acrylates Copolymer, Carbomer, Acrylates/C10-30 Alkyl Acrylate Crosspolymer, Acrylates/Beheneth-25 Methacrylate Copolymer, Sodium Acrylate/Sodium Acryloyldimethyl Taurate Copolymer, Acrylates/Vinyl Neodecanoate Crosspolymer, Hydroxypropyl Methylcellulose, Hydroxyethyl Cellulose, Polyurethane-79), waxes (such as Cera Alba (Beeswax), *Euphorbia* Cerifera (Candelilla) Wax, Copernicia Prunifera (Carnauba) Wax, Microcrystalline Wax), emulsifiers (such as Ceteareth-12, PEG-100 Stearate, Glyceryl Stearate, *Brassica* Glycerides, *Brassica* Alcohol, Laureth-4, Potassium Cetyl Phosphate), emollients (such as Petrolatum, Mineral Oil, Sunflower Oil, Squalene, Almond Oil), humectants (such as Glycerin, Urea, Betaine), pH-adjusters, antioxidants, fragrance, multi-functional ingredients, preservation technologies, and combinations thereof. In some embodiments, the formulation is a sunscreen.

Other components may be provided including those known in the art of sunscreen formulations, or for use in personal care compositions such as cosmetics. The compositions may include, optionally, for example, surfactants, buffers, perfumes, colorants, dyes, viscosity modifiers, water, oils, emulsifiers, preservatives, antioxidants, emollients, thickeners, gellants, vitamins, humectants, alcohols, botanical extracts and powders. Other suitable additive or components may include one or more oils in the product, such as, for example, almond oil, castor oil, coconut oil, corn (maize) oil, cottonseed oil, canola oil, flax seed oil, hempseed oil, nut oil, olive oil, palm oil, peanut oil, safflower oil, sesame oil, soybean oil, sunflower oil, jojoba oil, or combinations of these oils.

Surfactants may be included in the personal care composition, such as, for example, an anionic surfactant, a zwitterionic surfactant, a cationic surfactant, a non-ionic surfactant, or combinations of these. Other exemplary components or additives may include, without limitation, lipids, additional alcohols, waxes, pigments, vitamins, fragrances, bleaching agents, antibacterial agents, anti-inflammatory agents, antimycotic agents, thickeners, gums, starches, chitosan, polymeric materials, cellulosic materials, glycerin, proteins, amino acids, keratin fibers, fatty acids, siloxanes, botanical extracts, abrasives and/or exfoliants (chemical or mechanical), anticaking agents, antioxidant agents, binders, biological additives, buffering agents, bulking agents, chelating agents, chemical additives, denaturants, external analgesics, film formers, humectants, opacifying agents, pH adjusters, preservatives, propellants, reducing agents, sunscreen agents, skin darkening agents, essential oils, skin sensates, or combinations of these.

The personal care composition of the invention may also include one or more optical brighteners as described in U.S. Patent Publication No. 2011/0104078 A1, incorporated herein by reference, and also including for example, a triazine-stilbene (di-, tetra- or hexa-sulfonated), a courmarin, an imidazoline, a diazole, a triazole, a benzoxazoline, and a biphenyl stilbene.

Also included within the scope of the invention is a method of protecting skin, hair, and/or nails of a mammal from damage caused by exposure to light in the UV wavelengths by applying to the skin, hair or nails a composition as described above. "Skin" includes the external integument of living mammals, reptiles, amphibians, birds and other animals as well as processed skins, such as leathers or suedes. "Hair" includes hair, fur, wool and other filamentous keratinized structures of mammals and other animals. Similarly, "nails" includes claws, hooves and analogous structures of mammals and other animals.

Also within the scope of the invention are methods to improve the aesthetics of photoprotective formulations by using the composition so as to avoid a feeling of oiliness and/or greasiness without substantial loss or separation of ingredients when skin is damp, moist or otherwise wet.

Formulations.

In some embodiments, the present invention is directed to dispersion compositions including metal oxide particles that may be used in formulations for various applications. The dispersion composition or formulation is, or may be a component of, a personal care product, a home care product, a textile care product, an institutional care product, a pharmaceutical product, a veterinary product, a food product, or an industrial product. In some embodiments, the compositions may be used in formulations, or may be a component of, a personal care product. Personal care products include a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer. In preferred embodiments, the formulation is a sunscreen.

Formulations herein can be used, for example, as skin protection cream, facial moisturizer, sunscreen lotion, nourishing cream, day cream or night cream. Typical embodiments are creams, gels, e.g., but not limited to hydrogels, hydrodispersion gels, oil gels; lotions, alcoholic and aqueous/alcoholic solutions, emulsions in their various forms for example but not limited to oil in water (O/W), water in oil (W/O), mixed emulsions, PIT emulsions, Pickering emulsions, microemulsions, nano-emulsions; aerosol foams, non-aerosol foams, aerosol sprays, non-aerosol sprays, pump sprays, serums, roll-ons, pastes, balsams, or stick preparations. These compositions may also comprise, as further auxiliaries and additives, mild surfactants, co-emulsifiers, super fatting agents, pearlescent waxes, bodying agents, thickeners, polymers, silicone compounds, fats, waxes, stabilizers, biogenic active ingredients, deodorant active ingredients, antidandruff agents, film formers, swelling agents, hydrotropic agents, preservatives, insect repellants, tanning agents, artificial self-tanning agents (e.g. dihydroxyacetone), stabilizers, perfume oils, dyes, antimicrobial agents, aqueous and non-aqueous plant extracts and the like. The amounts of cosmetic or dermatological auxiliaries and carrier substances and perfume which can be used in each case can be determined by a person skilled in the art depending on the nature of the product in question. In a preferred embodiment according to the invention, the composition is a suncare formulation or sunscreen with an SPF of 30 or more. SPF is determined according to the standard ISO 24444:2019 "In Vivo Determination of the Sun Protection Factor (SPF)" and as regulated in "Over-the-counter sunscreen drug products; required labeling based on effectiveness testing" Food and Drug Administration, Code of Federal Regulations, Title 21, § 201.327.

In some embodiments, the sunscreen active agent(s) and/or metal oxides is/are present in the formulation in an amount effective to provide sunscreen protection consistent with the desired SPF of the composition and can be from about 0.5% to about 75% of the composition, preferably about 5% to about 70% of the composition by weight, and most preferably about 10% to about 40% of the composition by weight, although the amount may be adjusted for desired end effects and based on the selected active ingredients as is known in the art.

In some cases, the disclosed compositions may expressly exclude one or more of the aforementioned ingredients in this section, e.g., via claim language. For example claim language may be modified to recite that the disclosed compositions, formulations, processes, etc., do not utilize or comprise one or more of the aforementioned optional ingredients.

These detailed descriptions serve to exemplify the above general descriptions and embodiments which form part of the invention. These detailed descriptions are presented for illustrative purposes only and are not intended as a restriction on the scope of the invention.

Examples

Dispersion Preparation. Examples of MOP dispersions and Comparative Examples were prepared according to the following procedure. The ester dispersing medium and polyester dispersing agent were charged to an appropriately sized glass beaker and heated with gentle mixing until the polyester was liquefied (ca. 50-60° C.). The ester and polyester were mixed at 2000-2500 rpm using a Silverson L5M-A high shear rotor/stator laboratory for approximately one minute or until a clear (transparent) and homogenous solution was obtained. The MOP was added to the ester-polyester mixture and mixed at 5000-5500 rpm for five minutes to obtain a uniform dispersion. In general, mixing speed was adjusted as necessary according to dispersion viscosity. Care was taken to ensure that all MOP was uniformly incorporated into the dispersion and that no undispersed MOP was present.

Brookfield Viscosity Determination. A Brookfield Model DV1 Digital Viscometer was used to determine dispersion viscosity. Spindle and rotation speed were selected to ensure viscosity readings were taken within a torque window of 10-80% of the maximum torque range. For most dispersions viscosities were recorded using RV Spindle 3 at a rotation speed of 10-100 rpm.

Kinematic Viscosity Determination. An Anton Paar Stabinger Viscometer, Model SVM 3001, fulfilling the requirements of ASTM method D7042 was used to determine kinematic viscosities in cSt (Centistokes).

Rheological Parameters. Rheological parameters $G'_{plateau}$, $G''_{freq}$, Yield Stress, and Viscosities at 0.1 $s^{-1}$ and at 1 $s^{-1}$ were measured using a TA Instruments Discovery HR-20 rheometer using a standard 50 mm cone-plate geometry with 2° angle and a gap of 52 m, at a Peltier-controlled temperature of 25° C. Yield Stress values are determined with the modulus crossover method from an amplitude sweep test (at 1 rad/s) with $$\text{Yield Stress} = \frac{\%\ \text{strain}_{crossover}}{100}.$$

$\sqrt{2G'_{crossover}}$ with % $\text{strain}_{crossover}$ and $G'_{crossover}$ being the values for which G' and G" cross each other, i.e. $G'_{crossover}=G''_{crossover}$. [See, e.g., Utracki L A, Schlund B (1987) *Linear low density polyethylenes and their blends*. Part 2. Shear flow of LLDPE's. Polym Eng Sci 27:367-379; and Vega J F, Muñoz-Escalona A, Santamaría A, Muñoz M E, Lafuente P (1996) Comparison of the rheological properties of metallocene-catalyzed and conventional high-density polyethylenes. Macromolecules 29:960-965.] The plateau value of the storage modulus G', $G'_{plateau}$, and the amplitude range with a linear response (needed for the frequency sweep test) were also determined with the amplitude sweep test. The frequency dependence (kinetics of flow and relaxation) was determined with a frequency sweep test (at a % strain in the linear regime, 0.03% strain to 0.1% strain for the measured compositions) measuring both the storage (G') and loss modulus (G"). $G''_{freq}$ was determined from those measurements at a frequency of 1 rad/s. Viscosities and shear-thinning behavior are determined via flow curve measurements, i.e. viscosity vs shear rate ($s^{-1}$) measurements.

In vitro UV Transmission Measurements. The UV Transmission values of compositions containing metal oxide particles (MOPs) were measured using a Labsphere UV-2000 Ultraviolet Transmittance Analyzer for wavelength of 250-450 nm; the applied protocol compliant with US FDA Method (2011) for Broad Spectrum & UV1/UV determination. Specifically, 18.75 mg (milligram) of the composition was applied evenly to a 5×5 $cm^2$ polymethyl methacrylate (PMMA) plate. The treated plates rested for 15 minutes in a dark place before the transmission measurements. Transmittance was measured for five locations on each of three treated PMMA plates per composition (using an untreated PMMA plate as reference) and the average of these 15 measurements was used to determine the in vitro UV transmittance at 340 nm wavelength for that composition.

Dispersion Compositions. Table 1 shows dispersion compositions Examples E1 and E2 as well as for Comparative Examples CE1 and CE2 as prepared according to the method as described above and in the amounts as shown. Table 1 provides a comparison of unsaturated and branched esters versus saturated triglyceride esters.

Examples E1, E2 and Comparative Examples CE1, CE2

Unsaturated and Branched Esters (E1, E2) Versus Saturated Triglyceride Esters (CE1, CE2).

TABLE 1

Dispersion Compositions (E1, E2, CE1, and CE2)

| Component | INCI Name | Wt % in Dispersion E1 | E2 | CE1 | CE2 |
|---|---|---|---|---|---|
| MOP | Zinc Oxide | 50.05 | | | |
| Polyester | Polyhydroxystearic Acid | 2.00, 3.00, 4.00, 5.00, and 6.00 | | | |
| Ester | Heptyl Undecylenate | Q.S. to 100 wt % | | | |
| | Diisooctyl Succinate | | Q.S. to 100 wt % | | |
| | Triheptanoin | | | Q.S. to 100 wt % | |
| | Caprylic/Capric Triglyceride | | | | Q.S. to 100 wt % |

The MOP used in the dispersed metal oxide compositions in Table 1 was zinc oxide, Zano® 10 (EverCare). In amounts of 2.00 wt %, 3.00 wt %, 4.00 wt %, 5.00 wt % and 6.00 wt %, the polyester was polyhydrosystearic acid, Dispersun DSP-OL300 (Innospec). The weight ratio of MOP to ester in all compositions ranged from about 25:1 to about 8:1. These components were common to Examples E1 and E2 as well as for Comparative Examples CE1 and CE2, while the ester was varied.

Dispersion compositions for Example E1 were prepared with an unsaturated ester heptyl undecylenate, LexFeel™ Natural (INOLEX, Inc.). Dispersion compositions for Example E2 were prepared with a branched ester diisooctyl succinate, SustOleo™ DCS (INOLEX, Inc.). Comparative dispersion compositions for Example CE1 were prepared using saturated triglyceride ester triheptanoin, SustOleo™ MCT (INOLEX, Inc.). Comparative dispersion compositions for Example CE2 were prepared using saturated triglyceride ester caprylic/capric triglyceride Lexol® GT-865 (INOLEX, Inc.).

Dispersion viscosities for Examples E1 and E2 as well as for Comparative Examples CE1 and CE2 are shown in Table 2 for polyester amounts of 2.00 wt %, 3.00 wt %, 4.00 wt %, 5.00 wt %, and 6.00 wt %. The data, illustrated as a function of polyester concentration, is shown in FIG. 1.

Dispersion Viscosities as a Function of Polyester Concentration for (E1, E2) Versus (CE1, CE2).

TABLE 2

Dispersion Viscosities (cP).

| Polyester (wt %) | Ester: Heptyl Undecylenate E1 | Diisooctyl Succinate E2 | Triheptanoin CE1 | Caprylic/Capric Triglyceride CE2 |
|---|---|---|---|---|
| 2.00 | 321 | 2630 | 35200 | 6080 |
| 3.00 | 179 | 730 | 6340 | 4710 |
| 4.00 | 116 | 450 | 4930 | 1240 |
| 5.00 | 180 | 625 | 4600 | 2450 |
| 6.00 | 3730 | 3660 | 12960 | 7400 |

As shown in FIG. 1 and Table 2, Examples E1 and E2 exhibited significantly lower viscosity values versus Comparative Examples CE1 and CE2 across the entire range of polyester concentrations examined. The dispersion viscosities of Examples E1 and E2 were dramatically lower than those of Comparative Examples CE1 and CE2 in the optimal polyester range of 3.00 to 5.00 wt % where the lowest viscosity values were obtained at the MOP loading of 50.05 wt %.

These results demonstrated the surprising benefit of using unsaturated or branched esters for preparing low viscosity MOP dispersions compared to the saturated triglyceride esters that are conventionally employed for such dispersions.

As supplied ester dispersing medium data provided below in Table 3.

TABLE 3

| EDM Viscosities and Density. | | | |
|---|---|---|---|
| EDM | Density ($g/cm^3$) | Kinematic Viscosity (cSt) | Dynamic Viscosity (cP) |
| Heptyl Undecylenate (LexFeel ™ Natural, Inolex) | 0.867 | 5.7 | 4.9 |
| Diisooctyl Succinate (SustOleo ™ DCS, Inolex) | 0.920 | 11.9 | 10.9 |

Tables 4-6 detail example formulations, respectively. Examples E3-E5 use the ester dispersing medium (namely heptyl undecylenate as in E1 for E3, and diisooctyl succinate as in E2 for E4 and E5) combined with the polyhydroxystearic acid (4 wt %) as polyester dispersing agent, as described in the dispersion composition and characterization data according to Tables 1 and 2 above. Comparative example CE3 uses the ester dispersing medium (caprylic/capric triglyceride) as in CE2 and comparative examples CE4 and CE5 use the ester dispersing medium (triheptanoin) as in CEL. E3 and CE3 were made as water-in-oil (W/O) emulsions; E4 and CE4 were made as oil-in-water (O/W) emulsions, and E5 and CE5 were made as water-in-oil (W/O) emulsions.

The example sunscreen formulations were prepared as follows. Zinc oxide was dispersed into the blend of polyester (PHSA) and the selected ester as per the formulations detailed herein with homogenization at 1000 rpm for 1 minute and at 2500 rpm for 2 minutes (Silverson L5M-A, General Purpose Head). The remaining oil phase components were then added and heated to 70-75° C. while mixing with a propeller mixer at 100 rpm. In a separate vessel, main batch components were combined and heated to 70-75° C. while mixing with a propeller mixer at 100 rpm. The main batch components were then added into the oil phase with homogenization at 2500 rpm for 5 minutes. The formulation was then transferred to propeller mixing at 250 rpm, allowed to cool, where at 40° C. the remaining components were added and mixed further for 5 min. Mixing was continued until temperature reached ≤30° C.

TABLE 4

| Formulations including PHSA and an unsaturated EDM Ester (Example E3) versus a linear, saturated triglyceride ester (CE3) using (W/O) emulsions. | | | |
|---|---|---|---|
| Ingredient (INCI) | Trade Name (Supplier) | E3 Formula Wt % (as supplied) | CE3 Formula Wt % (as supplied) |
| | Oil Phase | | |
| Caprylic/Capric Triglyceride (and) Polyhydroxystearic Acid (and) Zinc Oxide | MOP dispersion CE2 with 4% PHSA | — | 50.66 |
| Heptyl Undecylenate (and) Polyhydroxystearic Acid (and) Zinc Oxide | MOP dispersion E1 with 4% PHSA | 50.66 | — |
| Polyglyceryl-3 Diisostearate | Lameform TGI (BASF) | 3.55 | 3.55 |
| Hydrogenated Rapeseed Oil | SustOleo TSB (INOLEX) | 1.01 | 1.01 |
| Capryloyl Glycerin/ Sebacic Acid Copolymer | LexFilm ™ Sun Natural MB (INOLEX) | 2.03 | 2.03 |
| | Main Batch | | |
| Water | Purified Water | 40.73 | 40.73 |
| Magnesium Sulphate | Magnesium Sulphate | 2.02 | 2.02 |
| | Total Wt % | 100.00 | 100.00 |

TABLE 5

| Formulations including PHSA and a branched EDM Ester (Example E4) versus a linear, saturated triglyceride ester (CE4) using (O/W) emulsions. | | | |
|---|---|---|---|
| Ingredient (INCI) | Trade Name (Supplier) | E4 Formula Wt % (as supplied) | CE4 Formula Wt % (as supplied) |
| | Main Batch | | |
| Water | Purified Water | 64.20 | 64.20 |
| Glycerin | Glycerin | 4.00 | 4.00 |
| Xanthan Gum | KELTROL ® CG (CP | 0.30 | 0.30 |

TABLE 5-continued

Formulations including PHSA and a branched EDM Ester (Example E4) versus a linear, saturated triglyceride ester (CE4) using (O/W) emulsions.

| Ingredient (INCI) | Trade Name (Supplier) | E4 Formula Wt % (as supplied) | CE4 Formula Wt % (as supplied) |
|---|---|---|---|
| | Kelco) | | |
| Caprylhydroxamic Acid (and) Methylheptylglycerin (and) Glycerin | Spectrastat ™ MHG Natural MB (Inolex) | 1.00 | 1.00 |
| | Oil Phase | | |
| Triheptanoin (and) Polyhydroxystearic Acid (and) Zinc Oxide | MOP dispersion CE1 with 4% PHSA | — | 20.00 |
| Diisooctyl Succinate (and) Polyhydroxystearic Acid (and) Zinc Oxide | MOP dispersion E2 with 4% PHSA | 20.00 | — |
| Arachidyl Alcohol (and) Behenyl Alcohol (and) Arachidyl Glucoside | Montanov ™ 202 (SEPPIC) | 5.00 | 5.00 |
| Hydroxyethyl Acrylate/Sodium Acryloyldimethyl Taurate Copolymer (and) Squalane (and) Polysorbate 60 | Simulgel ™ NS (SEPPIC) | 0.50 | 0.50 |
| Brassica Alcohol | SustOleo ™ BA (Inolex) | 2.00 | 2.00 |
| Capryloyl Glycerin/Sebacic Acid Copolymer | LexFilm ™ Sun Natural MB (Inolex) | 2.00 | 2.00 |
| Hydrogenated Rapeseed Oil | SustOleo ™ TSB (Inolex) | 1.00 | 1.00 |
| Total Wt % | | 100.00 | 100.00 |

TABLE 6

Formulations including PHSA and a branched EDM Ester (Example E5) versus a linear, saturated triglyceride ester (CE5) using (W/O) emulsions.

| Ingredient (INCI) | Trade Name (Supplier) | ES Formula Wt % (as supplied) | CE5 Formula Wt % (as supplied) |
|---|---|---|---|
| | Oil Phase | | |
| Triheptanoin (and) Polyhydroxystearic Acid (and) Zinc Oxide | MOP dispersion CE1 with 4% PHSA | — | 50.66 |
| Diisooctyl Succinate (and) Polyhydroxystearic Acid (and) Zinc Oxide | MOP dispersion E2 with 4% PHSA | 50.66 | — |
| Polyglyceryl-2 Dipolyhydroxystearate | Dehymuls PGPH (BASF) | 3.55 | 3.55 |
| Hydrogenated Rapeseed Oil | SustOleo TSB (INOLEX) | 1.01 | 1.01 |
| Capryloyl Glycerin/ Sebacic Acid Copolymer | LexFilm ™ Sun Natural MB (INOLEX) | 2.03 | 2.03 |
| | Main Batch | | |
| Water | Purified Water | 40.73 | 40.73 |
| Magnesium Sulphate | Magnesium Sulphate | 2.02 | 2.02 |
| Total Wt % | | 100.00 | 100.00 |

To show benefits of the invention, sunscreen formulations generated according to Tables 4-6 using different MOP dispersions were analyzed with respect to finished formulation viscosities and in vitro UV Transmission values. Importantly, the inventive examples, E3-E5, demonstrated lower viscosities and lower in vitro UV Transmission as compared with comparatives, CE3-CE5. It is desirable to create sunscreen formulations possessing both adequate sun protection properties (e.g., low UV Transmission values) by achieving high levels of well-dispersed ZnO particles in the formulation, while also providing improved sensory, tactile, and spreading behavior (e.g., reduced viscosity, storage and loss moduli, and yield stress values).

As detailed above, two types of sunscreen formulations were made, oil-in-water emulsions as in E4 and water-in-oil emulsions as in E3 and E5.

Table 7 shows data for inventive Examples (E3 to E5) and Comparative Examples (CE3 to CE5) (using the same PHSA) to study the impact of the different esters on rheological properties of finished sunscreen formulas using ZnO particle dispersions. The in vitro UV Transmission values were determined as well and are listed in Table 7.

TABLE 7

Rheology and UV Transmission Values for E3-E5 and Comparatives CE3-CE5.

| Example | Ester | Emulsion | $G'_{plateau}$ (Pa) | $G''_{freq}$ @ 1 rad/s (Pa) | Yield Stress (Pa) | Viscosity @ 0.1 $s^{-1}$ (cP) | Viscosity @ 1 $s^{-1}$ (cP) | In vitro UV Transmission (%) |
|---|---|---|---|---|---|---|---|---|
| E3 | Heptyl Undecylenate | W/O | 361 | 103 | 0.9 | 25,600 | 2,700 | 11.6 |
| CE3 | Caprylic/Capric Triglyceride | W/O | 2,068 | 643 | 4.4 | 45,000 | 4,200 | 26.1 |
| E4 | Diisooctyl Succinate | O/W | 1,266 | 326 | 12 | 101,000 | 23,200 | 38.1 |
| CE4 | Triheptanoin | O/W | 4,395 | 1,063 | 34 | 201,000 | 36,200 | 40.5 |
| E5 | Diisooctyl Succinate | W/O | 327 | 267 | 0.8 | 33,400 | 8,300 | 16.0 |
| CE5 | Triheptanoin | W/O | 3,125 | 454 | 7.0 | 102,764 | 10,000 | 21.7 |

The rheological parameters listed in Table 7 show that the viscosities, storage and loss moduli (G', G"), and yield stress values are all lower for the inventive examples versus the respective comparative example, i.e., the values for E3 are lower than for CE3, the values for E4 are lower than for CE4, and the values for E5 are lower than for CE5. Rheological parameters characterize a material with respect to its sensory, tactile, and spreading behavior. Sunscreen formulations typically are very thick, greasy, and difficult to spread, i.e. they exhibit high viscosities, storage and loss moduli, and yield stress values. It is desirable to create sunscreen formulations with adequate sun protection properties, but improved sensory, tactile, and spreading behavior. The inventive examples in Table 7 show this improved behavior over the respective comparative examples listed in the same table. Specifically, $G'_{plateau}$ is 3 to 9 times lower for the inventive examples versus the comparative examples, $G''_{freq}$ is 2 to 6 times lower, Yield Stress is 3 to 7 times lower, viscosity at 0.1 $s^{-1}$ is 1.5 to 3 times lower, and viscosity at 1 $s^{-1}$ is 17% to 60% lower. The quality of dispersion of the MOPs is important to achieve good sun protection and SPF values for a given use-level of MOPs. The in vitro UV Transmission values for the inventive examples are 22% to 55% lower compared to the in vitro UV Transmission values for the comparative examples. Table 8 lists the % reduction of rheology and UV transmittance parameters for the inventive examples E3 to E5 versus their respective comparative examples CE3 to CE5 as per $$\% \text{ reduction} = \frac{(x_{comparative} - x_{inventive})}{x_{comparative}} \cdot 100, \text{ with } x$$

being the parameter value for either the inventive or comparative example from Table 7 above.

TABLE 8

Percent Reduction of Rheology and UV Transmission parameters for Inventive Examples vs their Respective Comparative Examples.

| Example | % reduction of $G'_{plateau}$ | % reduction of $G''_{freq}$ | % reduction of Yield Stress | % reduction of visc. @ 0.1 $s^{-1}$ | % reduction of visc. @ 1 $s^{-1}$ | % reduction of UV Transmission |
|---|---|---|---|---|---|---|
| E3 vs. CE3 | 83 | 84 | 80 | 43 | 36 | 55 |
| E4 vs. CE4 | 71 | 69 | 66 | 50 | 36 | 22 |
| E5 vs. CE5 | 90 | 41 | 89 | 67 | 17 | 26 |
| Average Reduction | 81 | 65 | 78 | 53 | 30 | 34 |

Table 8 shows that the percent reduction of $G'_{plateau}$ is on average 81 percent for examples using a branched or unsaturated ester according to the invention as compared to a linear, saturated ester; the percent reduction of $G'_{freq}$ is on average 65 percent; the percent reduction of Yield Stress is on average 78 percent; the percent reduction of viscosity @0.1 $s^{-1}$ is on average 53 percent; the percent reduction of viscosity @1 $s^{-1}$ is on average 30 percent; and the percent reduction of UV Transmission is on average 34 percent. Sunscreen formulations according to embodiments herein provide reduced UV transmission (e.g., high SPF factor) while having increase spreadability.

Embodiments

The following embodiments, among others, are disclosed.

Clause 1. A nonaqueous composition for dispersing metal oxide particles, the composition comprising: an ester selected from the group consisting of:

(i) a liquid ester of Formula I:

I

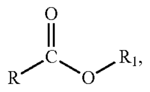

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

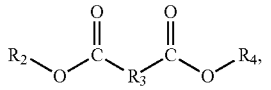

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

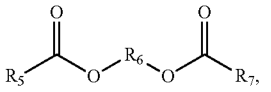

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof; and a polyester having a terminal carboxylic acid functional group.

Clause 2. The nonaqueous composition of clause 1, wherein the ester is of Formula I and R is a $C_5$-$C_{17}$ branched or cyclic alkyl, linear, branched, or cyclic alkenyl, or linear, branched, or cyclic alkynyl; and $R_1$ is a $C_3$-$C_{18}$ linear, branched, or cyclic alkyl, linear, branched, or cyclic alkenyl, or linear, branched, or cyclic alkynyl.

Clause 3. The nonaqueous composition of clause 1, wherein the ester is of Formula I and R and $R_1$ are different.

Clause 4. The nonaqueous composition of clause 1, wherein the ester is of Formula II and $R_2$ is a $C_3$-$C_{18}$ branched alkyl, linear or branched alkenyl, or linear or branched alkynyl; $R_3$ is a $C_2$-$C_8$ linear or branched alkyl, linear or branched alkenyl, or linear or branched alkynyl; and $R_4$ is a $C_3$-$C_{18}$ linear or branched alkyl, linear or branched alkenyl, or linear or branched alkynyl.

Clause 5. The nonaqueous composition of clause 1, wherein the ester is of Formula II and $R_2$ and $R_4$ are the same.

Clause 6. The nonaqueous composition of clause 1, wherein the ester is of Formula III and $R_5$ is a $C_3$-$C_{18}$ branched alkyl, linear or branched alkene, or linear or branched alkyne, $R_6$ is a $C_2$-$C_8$ linear or branched alkyl, linear or branched alkene, or linear or branched alkyne, and $R_7$ is a $C_3$-$C_{18}$ linear or branched alkyl, linear or branched alkene, or linear or branched alkyne.

Clause 7. The nonaqueous composition of clause 1, wherein the ester is of Formula III and $R_5$ and $R_7$ are the same.

Clause 8. The nonaqueous composition of clause 1, wherein the ester is liquid at 25° C.

Clause 9. The nonaqueous composition of clause 1, wherein the ester has a viscosity of less than about 100 cSt at 25° C.

Clause 10. The nonaqueous composition of clause 1, wherein carbon present in the ester is 100% biobased.

Clause 11. The nonaqueous composition of clause 1, wherein the polyester comprises a terminal single carboxylic acid functional group.

Clause 12. The nonaqueous composition of clause 1, wherein the polyester comprises two terminal carboxylic acid functional groups.

Clause 13. The nonaqueous composition of clause 1, wherein the polyester comprises a homopolymer derived from AB hydroxycarboxylic acid monomers.

Clause 14. The nonaqueous composition of clause 1, wherein the polyester comprises a copolymer derived from AA diol and BB diacid or dibasic ester monomers.

Clause 15. The nonaqueous composition of clause 1, wherein the polyester has a number-average molecular weight ($M_n$) of less than about 10,000 g/mol.

Clause 16. The nonaqueous composition of clause 1, wherein the polyester has an Acid Value of at least 15 mg KOH/g.

Clause 17. The nonaqueous composition of clause 1, wherein the polyester is selected from the group consisting of: Polyhydroxystearic Acid, Polyhydroxystearic Acid Stearate, Polyhydroxystearyl Succinate, Polyhydroxystearyl Sebacate, and combinations thereof.

Clause 18. The nonaqueous composition of clause 1, wherein carbon present in the polyester is 100% biobased.

Clause 19. A nonaqueous composition for dispersing metal oxide particles, the composition consisting essentially of: an ester selected from the group consisting of:

(i) a liquid ester of Formula I:

I

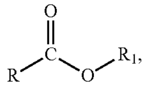

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

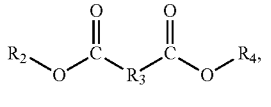

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

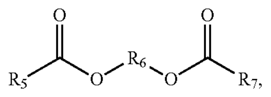

wherein R5 is a branched alkyl, a linear or branched alkene, or a linear or branched alkyne, R6 is a linear or branched alkyl, a linear or branched alkene, or a linear or branched alkyne, and R7 is a linear or branched alkyl, a linear or branched alkene, or a linear or branched alkyne; and (iv) combinations thereof; and a polyester having a terminal carboxylic acid functional group.

Clause 20. A nonaqueous composition for dispersing metal oxide particles, the composition consisting of: an ester selected from the group consisting of:

(i) a liquid ester of Formula I:

I

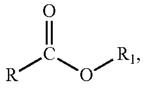

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

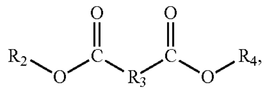

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

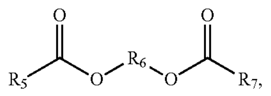

wherein R5 is a branched alkyl, a linear or branched alkene, or a linear or branched alkyne, R6 is a linear or branched alkyl, a linear or branched alkene, or a linear or branched alkyne, and R7 is a linear or branched alkyl, a linear or branched alkene, or a linear or branched alkyne; and (iv) combinations thereof; and a polyester having a terminal carboxylic acid functional group.

Clause 21. A nonaqueous dispersion comprising the nonaqueous composition of clause 1 and metal oxide particles dispersed therein.

Clause 22. The nonaqueous dispersion of clause 21, wherein the metal oxide particles are not surface-modified.

Clause 23. The nonaqueous dispersion of clause 21, wherein the metal oxide particles comprise zinc oxide, titanium oxide, or combinations thereof.

Clause 24. The nonaqueous dispersion of clause 21 having a viscosity of less than about 1000 cP.

Clause 25. The nonaqueous dispersion of clause 21, wherein the metal oxide particles comprise about 15 wt % to about 75 wt % of the nonaqueous dispersion.

Clause 26. The nonaqueous dispersion of clause 21, wherein the weight balance of the nonaqueous dispersion is comprised of the nonaqueous composition of claim 1.

Clause 27. The nonaqueous dispersion of clause 21, wherein the metal oxide particles comprise about 40 wt % to about 60 wt % of the nonaqueous dispersion.

Clause 28. The nonaqueous dispersion of clause 21, wherein the polyester is present in an amount of about 3 wt % to about 5 wt % based on total weight of the dispersion.

Clause 29. The nonaqueous dispersion of clause 21, wherein the nonaqueous dispersion is substantially devoid of silicones.

Clause 30. A nonaqueous dispersion comprising: a composition comprising: an ester selected from the group consisting of:

(i) a liquid ester of Formula I:

I

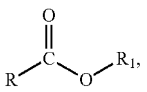

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

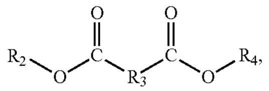

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

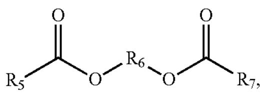

wherein R5 is a branched alkyl, a linear or branched alkene, or a linear or branched alkyne, R6 is a linear or branched alkyl, a linear or branched alkene, or a linear or branched alkyne, and R7 is a linear or branched alkyl, a linear or branched alkene, or a linear or branched alkyne; and (iv) combinations thereof; and a polyester having a terminal carboxylic acid functional group; and a plurality of metal oxide particles dispersed in the composition.

Clause 31. A formulation comprising the dispersion of any of clauses 21 or 30, wherein the formulation is or is a component of a personal care product selected from the group consisting of: a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, and a skin lotion or moisturizer.

Clause 32. The formulation of clause 31, wherein the formulation is or is a component of a sunscreen.

Clause 33. The formulation of clause 31, wherein the formulation is an oil-in-water (O/W) emulsion or a water-in-oil (W/O) emulsion.

Clause 34. The formulation of clause 31, further comprising at least one additional ingredient selected from the group consisting of film-forming polymers, rheology modifying polymers, waxes, emulsifiers, emollients, humectants, pH-adjusters, antioxidants, fragrance, multi-functional ingredients, preservation technologies, and combinations thereof.

Clause 35. A process for preparing a nonaqueous composition for dispersing metal oxide particles, the process comprising: mixing: an ester selected from the group consisting of:

(i) a liquid ester of Formula I:

I

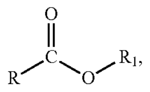

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

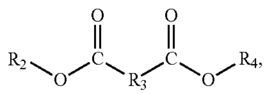

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

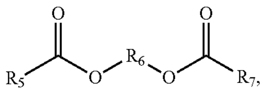

wherein R5 is a branched alkyl, a linear or branched alkene, or a linear or branched alkyne, R6 is a linear or branched alkyl, a linear or branched alkene, or a linear or branched alkyne, and R7 is a linear or branched alkyl, a linear or branched alkene, or a linear or branched alkyne; and (iv) combinations thereof; and a polyester having a terminal carboxylic acid functional group to form a homogeneous solution.

Clause 36. The process of clause 35, wherein the ester is of Formula I and R is a $C_5$-$C_{17}$ branched or cyclic alkyl, linear, branched, or cyclic alkenyl, or linear, branched, or cyclic alkynyl; and $R_1$ is a $C_3$-$C_{18}$ linear, branched, or cyclic alkyl, linear, branched, or cyclic alkenyl, or linear, branched, or cyclic alkynyl.

Clause 37. The process of clause 35, wherein the ester is of Formula I and R and $R_1$ are different.

Clause 38. The process of clause 35, wherein the ester is of Formula II and $R_2$ is a $C_3$-$C_{18}$ branched alkyl, linear or branched alkenyl, or linear or branched alkynyl, $R_3$ is a $C_2$-$C_8$ linear or branched alkyl, linear or branched alkenyl, or linear or branched alkynyl; and $R_4$ is a $C_3$-$C_{18}$ linear or branched alkyl, linear or branched alkenyl, or linear or branched alkynyl.

Clause 39. The process of clause 35, wherein the ester is of Formula II and $R_2$ and $R_4$ are the same.

Clause 40. The process of clause 35, wherein the ester is of Formula III and $R_5$ is a $C_3$-$C_{18}$ branched alkyl, linear or branched alkene, or linear or branched alkyne, $R_6$ is a $C_2$-$C_8$ linear or branched alkyl, linear or branched alkene, or linear or branched alkyne, and $R_7$ is a $C_3$-$C_{18}$ linear or branched alkyl, linear or branched alkene, or linear or branched alkyne.

Clause 41. The process of clause 35, wherein the ester is of Formula III and $R_5$ and $R_7$ are the same.

Clause 42. The process of clause 35, wherein the ester has a viscosity of less than about 100 cSt at 25° C.

Clause 43. The process of clause 35, wherein carbon present in the ester is 100% biobased.

Clause 44. The process of clause 35, wherein the polyester comprises a terminal single carboxylic acid functional group.

Clause 45. The process of clause 35, wherein the polyester comprises two terminal carboxylic acid functional groups.

Clause 46. The process of clause 35, wherein the polyester has a number-average molecular weight ($M_n$) of less than about 10,000 g/mol.

Clause 47. The process of clause 35, wherein the polyester has an Acid Value of at least 15 mg KOH/g.

Clause 48. The process of clause 35, wherein the polyester is chosen from the group consisting of Polyhydroxystearic Acid, Polyhydroxystearic Acid Stearate, Polyhydroxystearyl Succinate, Polyhydroxystearyl Sebacate, and combinations thereof.

Clause 49. The process of clause 35, wherein carbon present in the polyester is 100% biobased.

Clause 50. The process of clause 35, wherein mixing to form a homogeneous solution includes heating.

Clause 51. The process of clause 35, wherein mixing to form a homogeneous solution includes high-shear mixing.

Clause 52. The process of clause 35, further comprising dispersing metal oxide particles in the homogeneous solution to form a nonaqueous dispersion.

Clause 53. The process of clause 52, wherein the metal oxide particles comprise zinc oxide, titanium oxide, or combinations thereof.

Clause 54. The process of clause 52, wherein the nonaqueous dispersion has a viscosity of less than about 1000 cP.

Clause 55. The process of clause 52, wherein the metal oxide particles comprise about 15 wt % to about 75 wt % of the nonaqueous dispersion.

Clause 56. The process of clause 52, wherein the metal oxide particles comprise about 40 wt % to about 60 wt % of the nonaqueous dispersion.

Clause 57. The process of clause 52, wherein the nonaqueous dispersion is substantially devoid of silicones.

Clause 58. The process of clause 52, further comprising adding at least one additional ingredient therein to form a formulation.

Clause 59. The process of clause 52, wherein the at least one additional ingredient is selected from the group consisting of film-forming polymers, rheology modifying polymers, waxes, emulsifiers, emollients, humectants, pH-adjusters, antioxidants, fragrance, multi-functional ingredients, preservation technologies, and combinations thereof.

Clause 60. The process of clause 52, wherein the formulation is a sunscreen.

The present invention is not to be limited in scope by the specific embodiments described herein. Indeed, various modifications of the invention in addition to those described herein will be apparent to those skilled in the art from the foregoing description and figures. Such modifications are intended to fall within the scope of the appended claims.

It is further to be understood that all values are approximate and are provided for description. All references cited and discussed in this specification are incorporated herein by reference in their entirety and to the same extent as if each reference were individually incorporated by reference.

REFERENCES CITED

C. Agbo et al., *A Review on the Mechanism of Pigment Dispersion*, J. Disp. Sci. Tech., 2018, 39(6), 874-889

D.A. Brune et al., *Model for the Viscosity of Particle Dispersions; Journal of Macromolecular Science*—Rev. Macromol. Chem. Phys., C39(4), 561-642 (1999).

B. J. Naden et al. *Adsorption of poly(hydroxystearic acid) to $TiO_2$ nanoparticles, studied using gel permeation chromatography*, Coll. Surf. A.: Physicochem. Eng. Aspects, 2015, 478, 36-44.

Zinc oxide (nano form); What are the properties of ZnO nanoparticles?, https://ec.europa.eu/health/scientific-_committees/opinions_layman/zinc-oxide/de/1-3/3.htm#

Utracki LA, Schlund B (1987) *Linear low density polyethylenes and their blends*. Part 2. Shear flow of LLDPE's. Polym Eng Sci 27:367-379.

Vega J F, Muñoz-Escalona A, Santamaría A, Muñoz M E, Lafuente P (1996) *Comparison of the rheological properties of metallocene-catalyzed and conventional high-density polyethylenes*. Macromolecules 29:960-965.

U.S. Pat. No. 9,254,398 B2.

U.S. Patent Publication No. 2011/0104078 A1.

What is claimed is:

1. A nonaqueous composition for dispersing metal oxide particles, the nonaqueous composition consisting of:

an ester selected from the group consisting of:

(i) a liquid ester of Formula I:

I

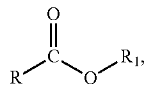

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

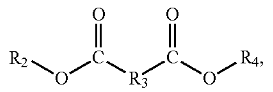

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

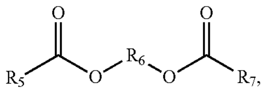

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof;

and a polyester having a terminal carboxylic acid functional group.

2. The nonaqueous composition of claim 1, wherein the ester is selected from the group consisting of:

Formula I and R is a $C_5$-$C_{17}$ branched or cyclic alkyl, linear, branched, or cyclic alkenyl, or linear, branched, or cyclic alkynyl; and $R_1$ is a $C_3$-$C_{18}$ linear, branched, or cyclic alkyl, linear, branched, or cyclic alkenyl, or linear, branched, or cyclic alkynyl;

Formula II and $R_2$ is a $C_3$-$C_{18}$ branched alkyl, linear or branched alkenyl, or linear or branched alkynyl; $R_3$ is a $C_2$-$C_8$ linear or branched alkyl, linear or branched alkenyl, or linear or branched alkynyl; and $R_4$ is a $C_3$-$C_{18}$ linear or branched alkyl, linear or branched alkenyl, or linear or branched alkynyl;

Formula III and $R_5$ is a $C_3$-$C_{18}$ branched alkyl, linear or branched alkene, or linear or branched alkyne, $R_6$ is a $C_2$-$C_8$ linear or branched alkyl, linear or branched alkene, or linear or branched alkyne, and $R_7$ is a $C_3$-$C_{18}$ linear or branched alkyl, linear or branched alkene, or linear or branched alkyne;

and combinations thereof.

3. The nonaqueous composition of claim 1, wherein the ester is liquid at 25° C.

4. The nonaqueous composition of claim 1, wherein the ester has a viscosity of less than about 100 cSt at 25° C.

5. The nonaqueous composition of claim 1, wherein the polyester comprises: a terminal single carboxylic acid functional group; two terminal carboxylic acid functional groups; a homopolymer derived from AB hydroxycarboxylic acid monomers; a copolymer derived from AA diol and BB diacid or dibasic ester monomers; or combinations thereof.

6. The nonaqueous composition of claim 1, wherein the polyester has a number-average molecular weight ($M_n$) of less than about 10,000 g/mol and an Acid Value of at least 15 mg KOH/g.

7. The nonaqueous composition of claim 1, wherein the polyester is selected from the group consisting of: Polyhydroxystearic Acid, Polyhydroxystearic Acid Stearate, Polyhydroxystearyl Succinate, Polyhydroxystearyl Sebacate, and combinations thereof.

8. The nonaqueous composition of claim 1, wherein carbon present in the ester is 100% biobased and carbon present in the polyester is 100% biobased.

9. A nonaqueous dispersion comprising the nonaqueous composition of claim 1 and metal oxide particles dispersed therein, the nonaqueous dispersion having a viscosity of less than about 1000 cP.

10. The nonaqueous dispersion of claim 9, wherein the metal oxide particles are not surface-modified.

11. The nonaqueous dispersion of claim 9, wherein the metal oxide particles comprise zinc oxide, titanium oxide, or combinations thereof.

12. The nonaqueous dispersion of claim 9, wherein the nonaqueous dispersion includes a weight fraction of metal oxide particles in a range from 15 wt % to 75 wt % based on total weight of the nonaqueous dispersion.

13. The nonaqueous dispersion of claim 12, wherein the weight fraction ranges from about 40 wt % to about 60 wt % based on total weight of the nonaqueous dispersion.

14. A nonaqueous dispersion comprising:

a nonaqueous composition consisting of:

an ester selected from the group consisting of:

(i) a liquid ester of Formula I:

I

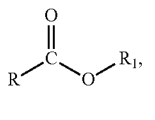

wherein R and $R_1$ are each a linear, branched, or cyclic alkyl; a linear, branched, or cyclic alkenyl; or a linear, branched, or cyclic alkynyl; wherein if one of R and $R_1$ is a linear alkyl, the other of R and $R_1$ is a branched, or cyclic alkyl; a linear, branched, or cyclic alkenyl; or a linear, branched, or cyclic alkynyl;

(ii) a liquid ester of Formula II:

II

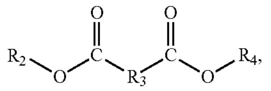

wherein $R_2$ is a branched alkyl, a linear or branched alkenyl, or a linear or branched alkynyl, $R_3$ is a linear or branched alkyl, a linear or branched alkenyl, or a linear or branched alkynyl, and $R_4$ is a linear or branched alkyl, a linear or branched alkenyl, or a linear or branched alkynyl;

(iii) a liquid ester of Formula III:

III

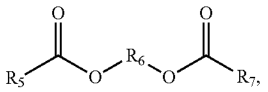

wherein $R_5$ is a branched alkyl, a linear or branched alkene, or a linear or branched alkyne, $R_6$ is a linear or branched alkyl, a linear or branched alkene, or a linear or branched alkyne, and $R_7$ is a linear or branched alkyl, a linear or branched alkene, or a linear or branched alkyne; and (iv) combinations thereof;

and a polyester having a terminal carboxylic acid functional group; and a plurality of metal oxide particles dispersed in the composition.

15. A formulation comprising the nonaqueous dispersion of claim 14, wherein the formulation is or is a component of a personal care product selected from the group consisting of: a cosmetic product; a conditioner of hair, nails, or skin; a shampoo; a hair styling product; an oil or wax for grooming facial hair; a permanent wave liquid; a hair colorant; a face or body wash; a makeup removal product; a cleansing lotion; an emollient lotion or cream; a bar soap; a liquid soap; a shaving cream, foam, or gel; a sunscreen; a gel, lotion, or cream for treating sunburn; a deodorant or anti-perspirant; a moisturizing gel; a face powder; a foundation; a lipstick; a blush; an eyeliner; a wrinkle or anti-aging cream; an eye shadow; an eyebrow pencil; a mascara; a mouthwash; a toothpaste; an oral care product; a skin cleansing product; a hair or fur cleansing product; and a skin lotion or moisturizer.

16. The formulation of claim 15, wherein the formulation is a sunscreen or is a component of a sunscreen.

17. The formulation of claim 15, wherein the formulation is an oil-in-water (O/W) emulsion or a water-in-oil (W/O) emulsion.

18. The nonaqueous dispersion of claim 14, wherein the liquid ester is heptyl undecylenate and the polyester is Polyhydroxystearic Acid.

19. The nonaqueous dispersion of claim 14, wherein the liquid ester is diisooctyl succinate and the polyester is Polyhydroxystearic Acid, wherein diisooctyl succinate is according to structure II-i:

II-i

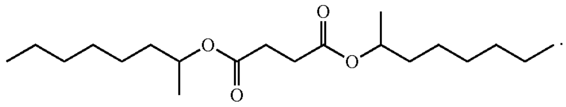

20. The nonaqueous composition of claim 1, wherein the liquid ester is heptyl undecylenate and the polyester is Polyhydroxystearic Acid.

21. The nonaqueous composition of claim 1, wherein the liquid ester is diisooctyl succinate and the polyester is Polyhydroxystearic Acid, wherein diisooctyl succinate is according to structure II-i:

II-i

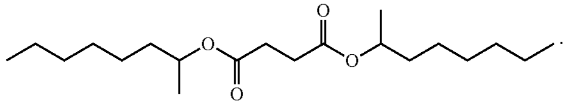

22. The nonaqueous composition of claim 1, wherein the nonaqueous composition has an ester:polyester ratio from 7.33:1 to 24:1 based on weight percent.

23. The nonaqueous composition of claim 22, wherein the nonaqueous composition has an ester:polyester ratio from 9:1 to 15.67:1 based on weight percent.

24. The nonaqueous dispersion of claim 14, wherein the nonaqueous composition has an ester:polyester ratio from 7.33:1 to 24:1 based on weight percent.

* * * * *